(12) United States Patent
Chan et al.

(10) Patent No.: US 7,486,402 B2
(45) Date of Patent: Feb. 3, 2009

(54) OPTICAL IMAGE MEASURING APPARATUS

(75) Inventors: Kinpui Chan, Yamagata (JP); Masahiro Akiba, Yamagata (JP)

(73) Assignee: Kabushiki Kaisha Topcon, Tokyo (JP)

( * ) Notice: Subject to any disclaimer, the term of this patent is extended or adjusted under 35 U.S.C. 154(b) by 351 days.

(21) Appl. No.: 11/240,450

(22) Filed: Oct. 3, 2005

(65) Prior Publication Data
US 2006/0072118 A1 Apr. 6, 2006

(30) Foreign Application Priority Data
Oct. 4, 2004 (JP) ............................. 2004-291243

(51) Int. Cl.
*G01B 9/02* (2006.01)
(52) U.S. Cl. ..................................... 356/495
(58) Field of Classification Search ................. 356/489, 356/495, 497
See application file for complete search history.

(56) References Cited

U.S. PATENT DOCUMENTS

| 5,459,570 | A | 10/1995 | Swanson et al. |
| 6,014,216 | A | 1/2000 | Zorabedian |
| 6,015,969 | A | 1/2000 | Nathel et al. |
| 6,385,358 | B1 * | 5/2002 | Everett et al. ................. 385/12 |

FOREIGN PATENT DOCUMENTS

| JP | 4-15046 | 1/1992 |
| JP | 6-165784 | 6/1994 |
| JP | 7-171140 | 7/1995 |
| JP | 2001-272335 | 10/2001 |
| JP | 2001-330558 | 11/2001 |

OTHER PUBLICATIONS

N. Tanno; "The imaging technic of the optical coherence tomography and its application to living organism image;" *Kogaku (Japanese Journal of Optics)*; vol. 28; No. 3; 1999; pp. 116-125 and Cover page (11 Sheets total)./Discussed in the specification.

(Continued)

*Primary Examiner*—Tarifur Chowdhury
*Assistant Examiner*—Jonathon D Cook
(74) *Attorney, Agent, or Firm*—Edwards Angell Palmer & Dodge LLP

(57) ABSTRACT

An optical image measuring apparatus including a light emitting portion outputting light having different wavelengths intensity-modulating the light periodically, a polarizing plate converting a light to linearly polarized light, a half mirror dividing the light into signal light and reference light, a wavelength plate converting a polarization characteristic of the reference light, a frequency shifter shifting a frequency of the reference light, the half mirror superimposing the signal light and the reference light on each other to produce interference light, a polarization beam splitter extracting a polarized light from the interference light, CCDs detecting the extracted polarized interference light, and a signal processing portion forming an image of an object to be measured based on the polarized interference light related to each of the lights, detected by the CCDs.

17 Claims, 10 Drawing Sheets

OTHER PUBLICATIONS

T. Nakajima; "Principle and application of the optical heterodyne method;" *Optical Heterodyne Technology*; 2003; pp. 1-10 and Cover page (7 Sheets total)./Discussed in the specification.

K.P. Chan, et al; "Micrometre-resolution, optical imaging of objects through highly scattered media using a heterodyne detector array;" *Electronics Letters*; vol. 30; No. 21; Oct. 13, 1994; pp. 1753-1754./Discussed in the specification.

European Search Report for EP Application No. 05020937.8, mailed Sep. 6, 2007.

Akiba et al. "Full-field optical coherence tomography by two-dimentional heterodyne detection with a pair of CCD cameras", Optics Letters, OSA, Optical Society of America, Washington, DC., vol. 28, No. 10, May 15, 2003, pp. 816-818.

Akiba et al, "Video-rate optical coherence imaging by two-dimentional heterodyne detection", Conference on Lasers and Electro-Optics. Technical Digest. Postconference Edition. Baltimore, MD., Trends in Optics and Photonics, Washington, WA., vol. 56, May 6, 2001, p. 380.

\* cited by examiner

FIRST PULSE SIGNAL

FRAME INTERVAL OF CCD

T: FRAME INTERVAL

SECOND PULSE SIGNAL

2T

FIRST LIGHT SOURCE DRIVE SIGNAL

SECOND LIGHT SOURCE DRIVE SIGNAL

T

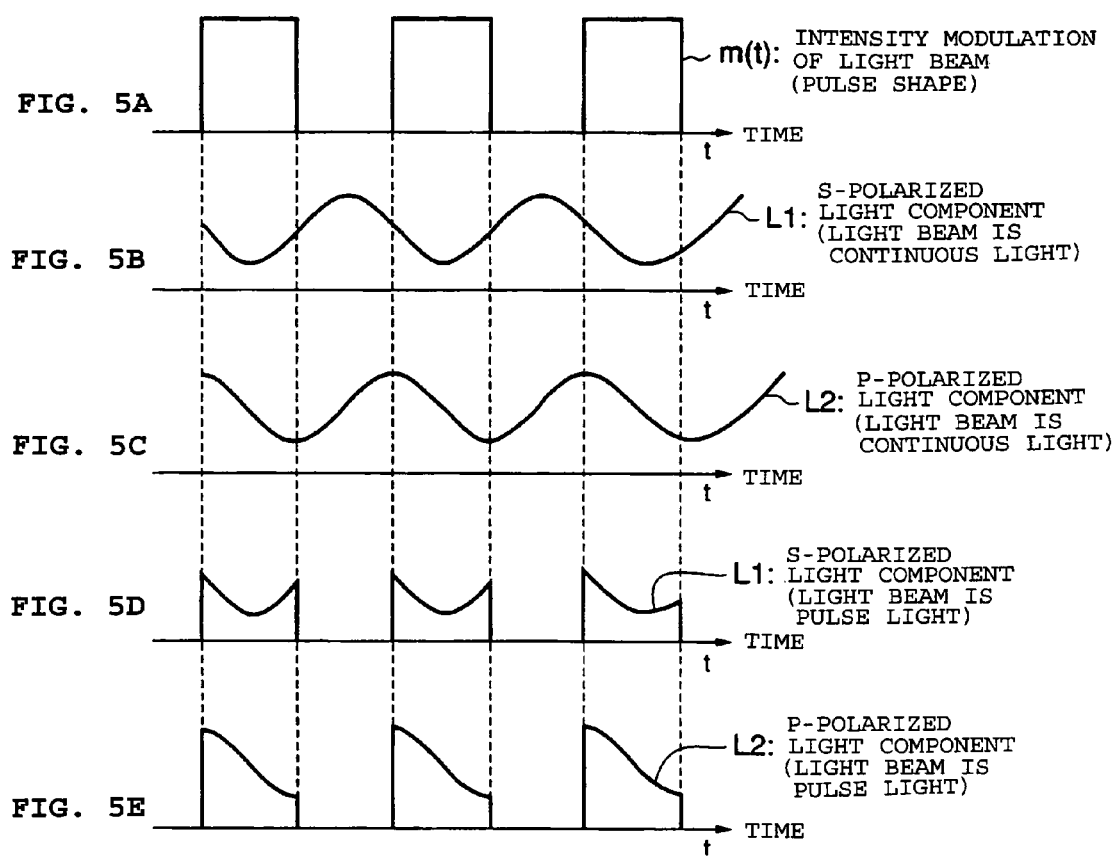

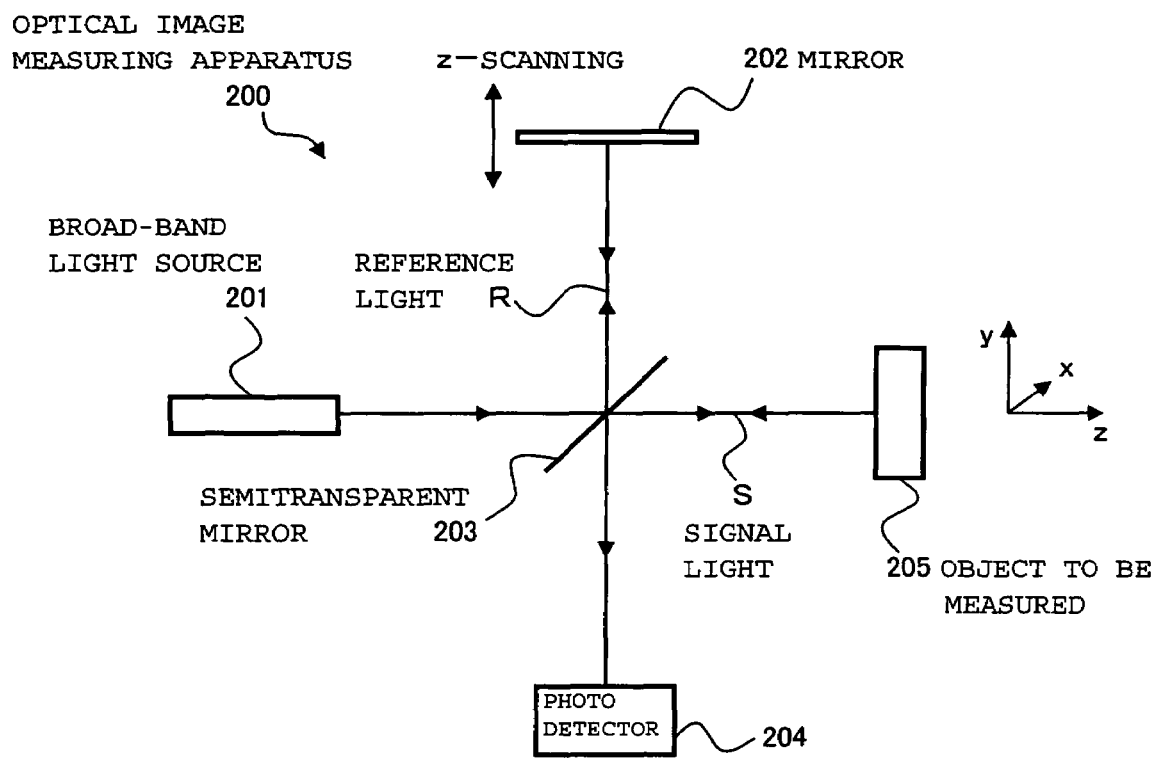

OPTICAL IMAGE MEASURING APPARATUS

Priority application Japanese Patent Application No. 2004-291243, filed Apr. 10, 2004, upon which this patent application is based is hereby incorporated by reference.

BACKGROUND OF THE INVENTION

1. Field of the Invention

The present invention relates to an optical image measuring apparatus that applies a light beam to an object to be measured, particularly a light scattering medium, and produces a surface form or inner form of the object to be measured by detecting a reflected light beam or a transmitted light beam. In particular, the present invention relates to an optical image measuring apparatus for measuring the surface form or inner form of the object to be measured by using an optical heterodyne detection method to produce the image of the measured form.

2. Description of the Related Art

In recent years, attention has been given to optical imaging technique that produces an image of a surface or inner portion of an object to be measured using a laser light source or the like. This optical imaging technique is not hazardous to human bodies in contrast to the conventional X-ray CT. Therefore, the development of applications in the medical field has been particularly expected.

An example of a typical method of the optical imaging technique is a low coherent interference method (also called 'optical coherence tomography' or the like). This method uses the low coherence of a broad-band light source having a broad spectral width, such as a super luminescent diode (SLD). According to this method, reflection light from an object to be measured or light transmitted therethrough can be detected at superior distance resolution on the order of μm (for example, see Naohiro Tanno, "Kogaku" (Japanese Journal of Optics), Volume 28, No. 3, 116 (1999)).

FIG. 9 shows a basic structure of a conventional optical image measuring apparatus based on a Michelson interferometer, as an example of an apparatus using the low coherent interference method. An optical image measuring apparatus 200 includes a broad-band light source 201, a mirror 202, a beam splitter 203, and a photo detector 204. An object to be measured 205 is made of a scattering medium. A light beam from the broad-band light source 201 is divided by the beam splitter 203 into two, that is, reference light R propagating to the mirror 202 and signal light S propagating to the object to be measured 205. The reference light R is light reflected by the beam splitter 203. The signal light S is light transmitted through the beam splitter 203.

Here, as shown in FIG. 9, a propagating direction of the signal light S is set as a z-axis direction and a plane orthogonal to the propagating direction of the signal light S is defined as an x-y plane. The mirror 202 is movable in a direction indicated by a double-headed arrow in FIG. 9 (z-scanning direction).

The reference light R is subjected to a Doppler frequency shift through when reflected by the z-scanning mirror 202. On the other hand, the signal light S is reflected from the surface of the object to be measured 205 and from the inner layers thereof when the object to be measured 205 is irradiated with the signal light S. The object to be measured 205 is made of the scattering medium, so reflection light of the signal light S may be a diffusing wave having random phases. The signal light propagating through the object to be measured 205 and the reference light that propagates through the mirror 202 to be subjected to the frequency shift are superimposed on each other by the beam splitter 203 to produce interference light.

In the image measurement using such a low coherent interference method, interference occurs only when a difference in optical path length between the signal light S and the reference light R is within the coherence length (coherent distance) on the order of μm of the light source. In addition, only the component of the signal light S whose phase is correlated to that of the reference light R interferes with the reference light R. That is, only the coherent signal light component of the signal light S selectively interferes with the reference light R. Based on their principles, the position of the mirror 202 is shifted by the z-scanning to vary the optical path length of the reference light R, so that a reflectance profile of the inner layers of the object to be measured 205 is measured. The object to be measured 205 is also scanned with the irradiated signal light S in an x-y plane direction. The interference light is detected by the photo detector 204 during such scanning in the z-direction and the x-y plane direction. An electrical signal (heterodyne signal) outputted as a detection result is analyzed to obtain a two-dimensional sectional image of the object to be measured 205 (see Naohiro Tanno, "Kogaku" (Japanese Journal of Optics), Volume 28, No. 3, 116 (1999)).

Assume that an intensity of the reference light R and an intensity of the signal light S which are superimposed by the beam splitter 203 are given by $I_r$ and $I_s$, respectively, and a frequency difference between the reference light R and the signal light S and a phase difference therebetween are given by $f_{if}$ and $\Delta\theta$, respectively. In this case, a heterodyne signal as expressed by the following expression is outputted from the photo detector (for example, see Yoshizawa and Seta "Optical Heterodyne Technology (revised edition)", New Technology Communications (2003), p.2).

Expression (1)

$$i(t) \propto I_r + I_s + 2\sqrt{I_r I_s} \cos(2\pi f_{if} t + \Delta\theta) \qquad (1)$$

The third term of the right side of the expression (1) indicates an alternating current electrical signal and the frequency $f_{if}$ thereof is equal to the frequency of beat caused from the interference between the reference light R and the signal light S. The frequency $f_{if}$ of an alternating current component of the heterodyne signal is called a beat frequency or the like. The first and second terms of the right side of the expression (1) indicate the direct current components of the heterodyne signal and correspond to a signal intensity of background light of interference light.

However, when the two-dimensional cross sectional image is obtained by the conventional low coherent interference method, it is necessary to scan the object to be measured 205 with a light beam and to successively detect reflection light waves from respective regions of the object to be measured 205 in a depth direction (z-direction) and a sectional direction (x-y plane direction). Therefore, the measurement of the object to be measured 205 requires a long time. In addition, it is hard to shorten a measurement time in view of measurement fundamentals.

In views of such problems, an optical image measuring apparatus for shortening a measurement time has been proposed. FIG. 10 shows a fundamental structure of an example of such an apparatus. As shown in FIG. 10, an optical image measuring apparatus 300 includes a broad-band light source 301, a mirror 302, a beam splitter 303, a two-dimensional photo sensor array 304 serving as a photo detector, and lenses 306 and 307. A light beam emitted from the light source 301 is converted into a parallel light flux by the lenses 306 and 307 and a beam diameter thereof is widened thereby. Then, the parallel light flux is divided into two, that is, the reference light R and the signal light S by the beam splitter 303. The reference light R is subjected to Doppler frequency shift through z-scanning with the mirror 302. On the other hand, the signal light S is incident on the object to be measured 305 over a broad area of the x-y plane because the beam diameter is widened. Therefore, the signal light S becomes reflection light including information related to the surface and inner portion of the object to be measured 305 over a wide area. The reference light R and the signal light S are superimposed on each other by the beam splitter 303 and detected by elements (photo sensors) arranged in parallel on the two-dimensional photo sensor array 304. Thus, it is possible to obtain a two-dimensional cross sectional image of the object to be measured 305 in real time without light beam scanning.

An apparatus described in K. P. Chan, M. Yamada, and H. Inaba, "Electronics Letters", Vol. 30, 1753 (1994) has been known as such a non-scanning type optical image measuring apparatus. In the apparatus described in the same document, a plurality of heterodyne signals outputted from a two-dimensional photo sensor array are inputted to signal processing systems arranged in parallel to detect the amplitude and phase of each of the heterodyne signals.

However, when the spatial resolution of an image is increased, it is necessary to increase a number of elements of the array. In addition, it is necessary to prepare a signal processing system including a number of channels corresponding to the number of elements. Therefore, it is supposedly hard to actually use the apparatus in fields that require a high resolution image, such as a medical field and an industrial field.

Thus, the inventors of the present invention have proposed the following non-scanning type optical image measuring apparatus in JP 2001-330558 A (claims and specification paragraphs [0044] and [0072] to [0077]). The optical image measuring apparatus according to this proposal includes a light source for emitting a light beam, an optical interference system, and a signal processing portion. In the optical interference system, the light beam emitted from the light source is divided into two, that is, signal light propagating through an examined object arrangement position in which an object to be examined is arranged and reference light propagating on an optical path different from an optical path passing through the examined object arrangement position. The signal light propagating through the examined object arrangement position and the reference light propagating on the different optical path are superimposed on each other to produce interference light. The optical interference system includes a frequency shifter, light cutoff devices, and photo sensors. The frequency shifter shifts a frequency of the signal light and a frequency of the reference light relative to each other. In order to receive the interference light in the optical interference system, the interference light is divided into two parts. The light cutoff devices periodically cut off the two divided parts of the interference light to generate two interference light pulse trains with a phase difference of 90 degrees therebetween. The photo sensors respectively receive the two interference light pulse trains. The photo sensors each have a plurality of detection elements which are spatially arranged and separately detect the interference light pulse trains. The signal processing portion combines the plurality of interference signals detected by the photo sensors to generate signals of the signal light which correspond to respective points of interest of a surface or inner layers of the object to be examined which is arranged in the examined object arrangement position along the propagation path of the signal light.

In the optical image measuring apparatus, the interference light in which the reference light and the signal light interfere with each other is divided into two parts. The two parts of the interference light are received by the two photo sensors (two-dimensional photo sensor arrays) and respectively sampled by the light cutoff devices (shutters) disposed in front of both sensor arrays. A phase difference of $\pi/2$ is set between sampling periods of the two divided parts of the interference light. Therefore, an intensity of the signal light and an intensity of the reference light which compose background light of the interference light and phase quadrature components (sine component and cosine component) of the interference light are detected. In addition, an intensity of the background light included in outputs from both the sensor arrays is subtracted from the outputs of both the sensor arrays to calculate two phase quadrature components of the interference light. An amplitude of the interference light is obtained based on the calculation result.

An available image sensor such as a charge-coupled device (CCD) camera has been widely used for the two-dimensional photo sensor array of the optical image measuring apparatus as described above. However, up to now, a problem has been recognized that a currently available CCD camera cannot follow the beat frequency of a heterodyne signal which is the order of several kHz to several MHz because of the low frequency response characteristic thereof. The feature of the optical image measuring apparatus which is proposed by the inventors of the present invention and described in JP 2001-330558 A (claims, specification paragraphs [0068] to [0084], and FIG. 1) is to perform the measurement using the low frequency response characteristic based on the sufficient recognition of the problem.

As described in JP 06-165784 A (claims, specification paragraphs [0019] to [0048], and FIG. 1), JP 2001-272335 A (claims, specification paragraphs [0026] and [0027], and FIG. 8), or the like, the optical image measuring apparatus is also used to obtain functional information such as the oxygen saturation of hemoglobin in the bloodstream of a living tissue which is an object to be measured.

The optical image measuring apparatus (optical tomographic imaging apparatus) disclosed in JP 06-165784 A includes: irradiating means for irradiating an object to be examined with light having at least two different wavelengths; reflection light beam detecting means for separately detecting light beams reflected on inner portions of the object to be examined in its depth direction, of the light with which the object to be examined is irradiated; first calculating means for performing calculation among different depth components of an output signal from the reflection light detecting means; second calculating means for performing the calculation among different wavelength components of the output signal from the reflection light detecting means; and imaging means for forming a tomographic image based on results outputted from the first and second calculating means. In particular, intensities of the reflected light beams are obtained using the light having the two different wavelengths as the light with which the object to be examined is irradiated. Further, the concentration of oxygen saturation or the like which becomes the functional information on the living tissue is calculated and a distribution image of the concentration thus calculated is displayed on a display device.

The optical image measuring apparatus (spectroscopic tomographic image measuring apparatus) disclosed in JP 2001-272335 A includes a broad-band wavelength light source, an irradiation optical system, a spatial delay Fizeau interferometer, a high-speed spectrometer, and an image data processing computer. A tomographic image from the spatial delay Fizeau interferometer is measured and simultaneously a wavelength spectrum of scattering light from the high-speed spectrometer is measured.

The optical image measuring apparatus described in JP 06-165784 A performs (one-dimensional) scanning with signal light which is condensed by a lens and with which the object to be measured is irradiated in a direction orthogonal to an irradiation direction of the signal light (see specification paragraph [0019]). According to this apparatus, enormous amounts of scanning and signal processing are required to form a two dimensional image of the object to be measured or a three-dimensional image thereof. Therefore, it is difficult for this apparatus to realize efficient image formation performed by the inventors of the present invention as described in JP 2001-330558 A.

As in the case of JP 06-165784 A, the optical image measuring apparatus described in JP 2001-272335 A also performs scanning with the condensed signal light to form an image of the object to be measured, so it is difficult to realize efficient measurement. This apparatus can be applied only to a Fizeau interferometer, so the degree of freedom of apparatus design is limited.

A pulse oximeter as described in JP 04-15046 A or JP 07-171140 A (specification paragraph [0022]) has been mainly used for conventional measurement of the oxygen saturation of hemoglobin. According to the pulse oximeter, the calculated oxygen saturation value is displayed on a display or printed on a sheet by a printer. However, the oxygen saturation is not displayed as an image.

SUMMARY OF THE INVENTION

The present invention has been made in view of the above-mentioned circumstances. An object of the present invention is to provide an optical image measuring apparatus capable of efficiently forming an image expressing functional information on a living tissue, such as the oxygen saturation of hemoglobin.

According to a first aspect of the present invention, there is provided an optical image measuring apparatus, including: light beam outputting means for selectively outputting one of a plurality of light beams having different wavelengths, intensities of the light beams being periodically modulated; first converting means for converting a polarization characteristic of the outputted one of the light beams to linear polarization; dividing means for dividing the outputted one of the light beams into signal light propagating through an object to be measured and reference light propagating through a reference object; second converting means for converting a polarization characteristic of one of the signal light and the reference light, which is the linear polarization; frequency shifting means for shifting a frequency of the signal light and a frequency of the reference light relative to each other; superimposing means for superimposing the signal light propagating through the object to be measured and the reference light propagating through the reference object on each other to produce interference light in which each of the signal light and the reference light includes a polarization characteristic converted by the first converting means and the second converting means and the frequency of the signal light and the frequency of the reference light are shifted by the frequency shifting means; extracting means for extracting a plurality of polarized light components from the produced interference light, the polarized light components being different from one another; two-dimensional detection means for detecting each of the polarized light components extracted from the interference light; and image forming means for forming an image of the object to be measured based on a result obtained by the two-dimensional detection means with respect to each of at least two light beams of the plurality of light beams having the different wavelengths. Therefore, when the wavelengths of the light beams used for image formation are set as appropriate, it is possible to obtain an image expressing functional information such as the oxygen saturation of hemoglobin. At this time, because the polarized light components of the interference light can be effectively detected using the two-dimensional detection means, a two-dimensional image of the object to be measured at a depth thereof is obtained at a time without being scanned with the signal light. Thus, it is unnecessary to perform scanning for obtaining the two-dimensional image unlike in conventional cases, so an image expressing the functional information on a living tissue can be efficiently formed.

According to a second aspect of the present invention, there is provided an optical image measuring apparatus, including: light beam outputting means for selectively outputting one of a plurality of light beams having different wavelengths; dividing means for dividing the outputted one of the light beams into signal light propagating through an object to be measured and reference light propagating through a reference object; frequency shifting means for shifting a frequency of the signal light and a frequency of the reference light relative to each other; superimposing means for superimposing the signal light propagating through the object to be measured and the reference light propagating through the reference object on each other to produce interference light in which the frequency of the signal light and the frequency of the reference light are relatively shifted; optical path dividing means for dividing an optical path of the produced interference light into a plurality of optical paths; intensity modulating means for modulating an intensity of an interference light beam propagating on each of the optical paths at a predetermined frequency; two-dimensional detection means for detecting the interference light beam whose intensity is modulated and which propagates on each of the optical paths; and image forming means for forming an image of the object to be measured based on a result obtained by the two-dimensional detection means with respect to each of at least two light beams of the plurality of light beams having the different wavelengths. Therefore, when the wavelengths of the light beams used for image formation are set as appropriate, it is possible to obtain an image expressing functional information such as the oxygen saturation of hemoglobin. At this time, because the interference light beam can be effectively detected using the two-dimensional detection means, a two-dimensional image of the object to be measured at a depth thereof is obtained at a time without being scanned with the signal light. Thus, it is unnecessary to perform scanning for obtaining the two-dimensional image unlike in conventional cases, so an image expressing the functional information on a living tissue can be efficiently formed.

BRIEF DESCRIPTION OF THE DRAWINGS

In the accompanying drawings:

FIGS. 4A to 4E are explanatory graphs showing an example of processing for generating light source drive signals for driving two broad-band light sources in the optical image measuring apparatus according to the first embodiment of the present invention, in which FIG. 4A illustrates a time waveform of a first pulse signal corresponding to a frequency for intensity modulation of a light beam, FIG. 4B illustrates a frame interval for detecting interference light beams by CCDs, FIG. 4C illustrates a time waveform of a second pulse signal corresponding to a frequency for switching between outputs from the two broad-band light sources, FIG. 4D illustrates a time waveform of a first light source drive signal outputted to one of the two broad-band light sources, and FIG. 4E illustrates a time waveform of a second light source drive signal outputted to the other of the two broad-band light sources;

FIGS. 5A to 5E are explanatory graphs showing interference light detection modes of the optical image measuring apparatus according to the first embodiment of the present invention, in which FIG. 5A illustrates a time waveform of a light beam whose frequency is intensity-modulated to be outputted from a broad-band light source, FIG. 5B illustrates a time waveform of an S-polarized light component of interference light in the case where the laser beam outputted from the broad-band light source is continuous light, FIG. 5C illustrates a time waveform of a P-polarized light component of the interference light in the case where the laser beam outputted from the broad-band light source is the continuous light, FIG. 5D illustrates a time waveform of the S-polarized light component of the interference light in the case where the intensity of the laser beam outputted from the broad-band light source is modulated, and FIG. 5E illustrates a time waveform of the P-polarized light component of the interference light in the case where laser beam outputted from the broad-band light source is intensity-modulated;

FIGS. 8A to 8C are explanatory graphs for explaining sampling operations of interference light beams which are performed by intensity-modulation means (shutters) of the optical image measuring apparatus according to the second embodiment of the present invention, in which FIG. 8A illustrates a time waveform of interference light, FIG. 8B illustrates a time waveform of an interference light beam received through one of the two intensity-modulation means, and FIG. 8C illustrates a time waveform of an interference light beam received through the other of the two intensity modulation means;

FIG. 9 is a schematic diagram showing a conventional optical image measuring apparatus.

DETAILED DESCRIPTION OF THE PREFERRED EMBODIMENTS

An example of an optical image measuring apparatus according to each of preferred embodiments of the present invention will be described in detail with reference to the accompanying drawings. Hereinafter, a first embodiment in which image measurement is performed using a polarization characteristic of light and a second embodiment in which image measurement is performed by sampling using shutters will be described. The optical image measuring apparatus is used to measure a tomographic image or a surface image of a living tissue or the like (object to be measured), for example, in medical fields.

First Embodiment

[Structure of Apparatus]

Figure 1:
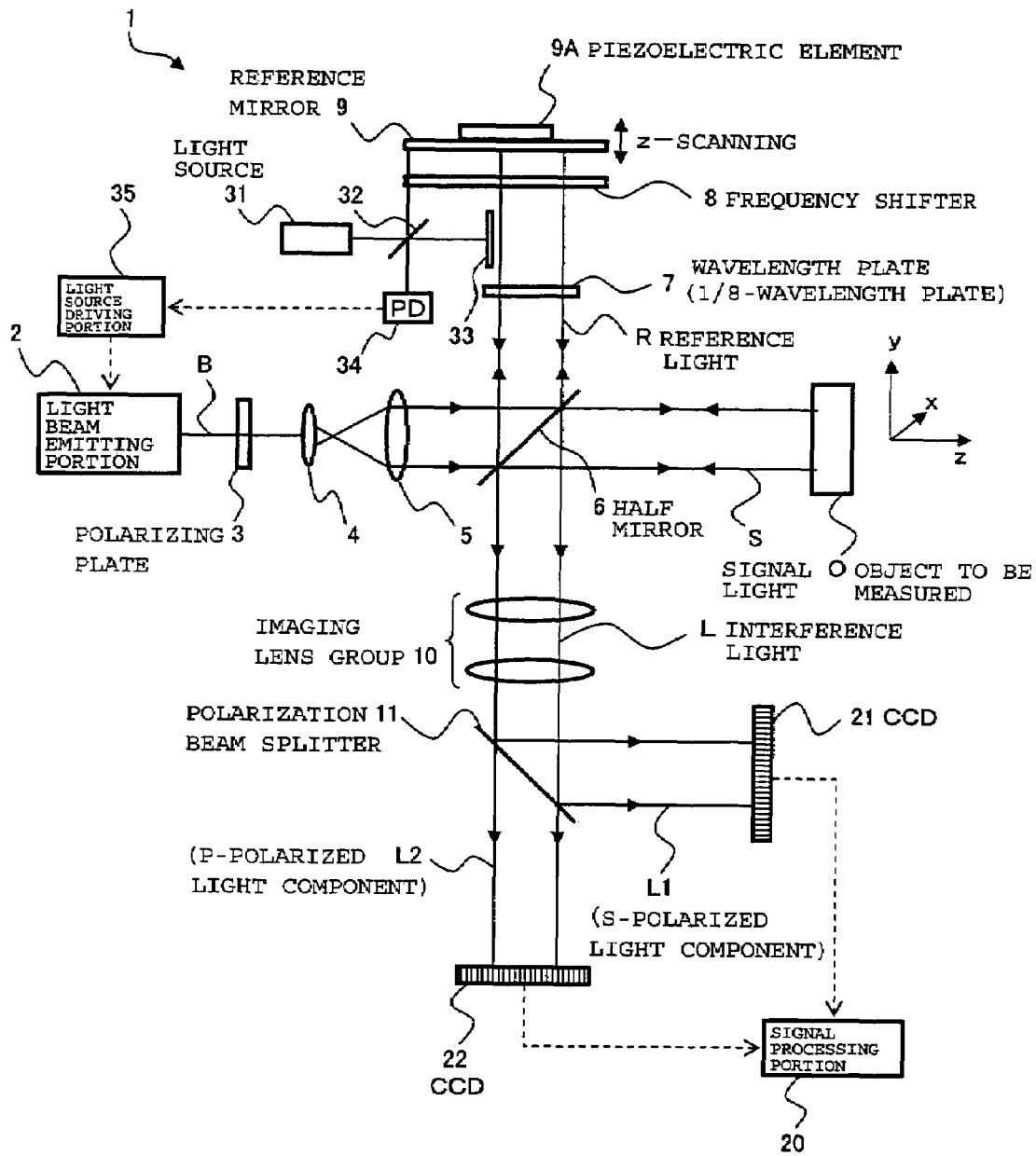
FIG. 1 is a schematic diagram showing an example of an optical system of an optical image measuring apparatus according to a first embodiment of the present invention.
Figure 2:
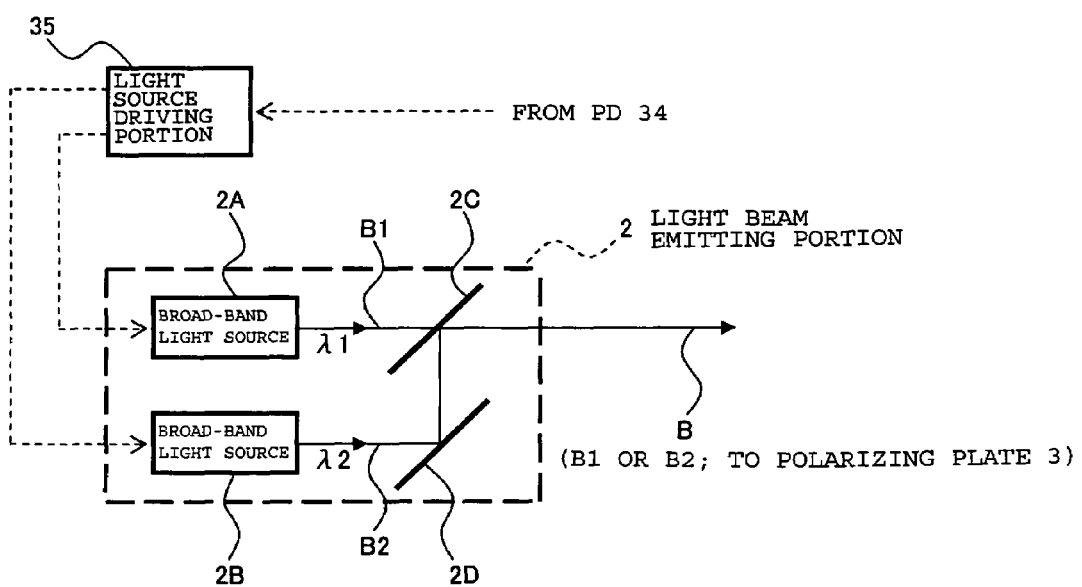
FIG. 2 is a schematic diagram showing an example of the optical system of the optical image measuring apparatus according to the first embodiment of the present invention.
Figure 3:
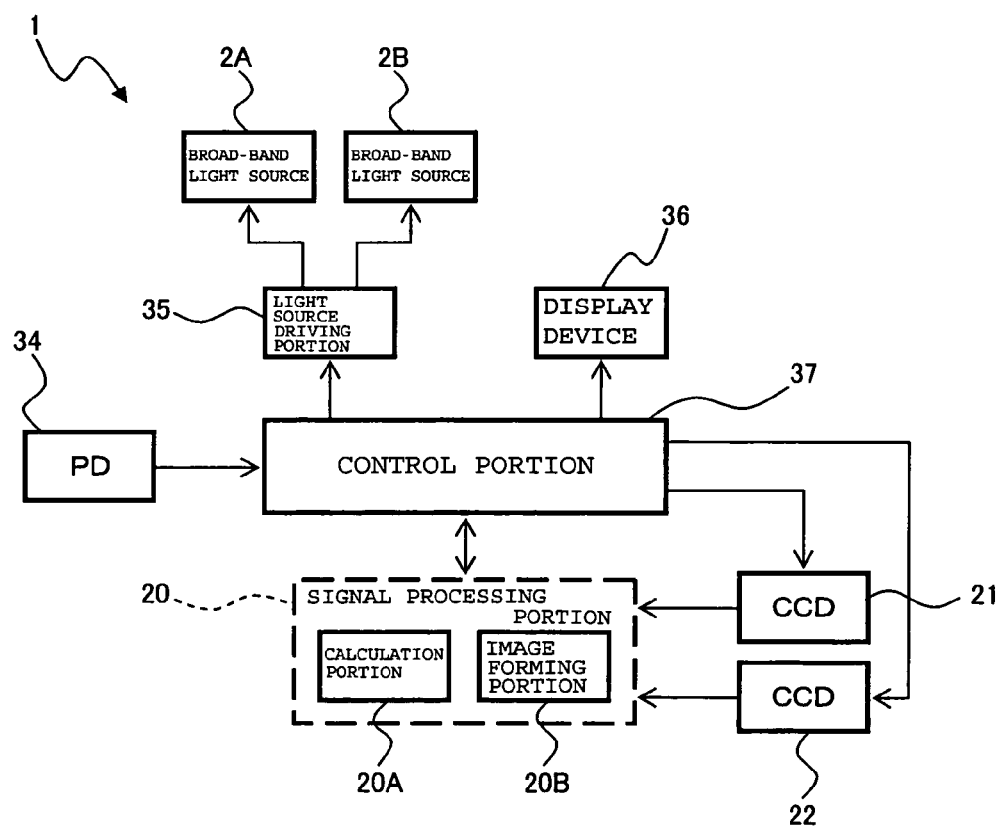
FIG. 3 is a schematic diagram showing an example of a control system of the optical image measuring apparatus according to the first embodiment of the present invention.

First, an optical image measuring apparatus according to the first embodiment of the present invention will be described in detail with reference to FIGS. 1 to 4. FIG. 1 illustrates a structure of (mainly) an optical system of an optical image measuring apparatus 1 according to this embodiment. FIG. 2 illustrates a structure of a light beam emitting portion 2 in the optical system of the optical image measuring apparatus 1. FIG. 3 illustrates a structure of a control system of the optical image measuring apparatus 1. FIGS. 4A to 4E are explanatory diagrams showing processing for generating drive signals for the light beam emitting portion 2 of the optical image measuring apparatus 1.

[Structure of Optical System]

As shown in FIG. 1, the optical image measuring apparatus 1 includes a light beam emitting portion 2 for selectively outputting one of a plurality of light beams having different wavelengths in which the intensities of the light beams are periodically modulated, a polarizing plate 3 for converting a polarization characteristic of a light beam B emitted from the light beam emitting portion 2 to linear polarization, lenses 4 and 5 for converting the light beam B to a parallel light beam and increasing a beam diameter thereof, and a half mirror 6 for dividing the light beam B into signal light S and reference light R and superimposing the signal light S and the reference light R on each other to produce interference light L. The optical image measuring apparatus 1 further includes a wavelength plate 7 for converting a polarization characteristic of the reference light R from linear polarization to circular polarization, a frequency shifter 8 for shifting a frequency of the reference light R, a reference mirror 9 for totally reflecting the reference light R on a reflective surface orthogonal to a propagating direction of the reference light R, and a piezoelectric element 9A provided on a rear surface of the reference mirror 9 which is opposite to the reflective surface thereof.

As shown in FIG. 2, the light beam emitting portion 2 includes broad-band light sources 2A and 2B, each of which outputs a low-coherent light beam. Light beams B1 and B2 outputted from the broad-band light sources 2A and 2B have wavelengths different from each other. Assume that (center) wavelengths of the light beams B1 and B2 are expressed by $\lambda 1$ and $\lambda 2$.

Each of the wavelengths $\lambda 1$ and $\lambda 2$ of the light beams B1 and B2 is set to, for example, the vicinity of 805 nm at which an absorption characteristic of oxyhemoglobin and an absorption characteristic of deoxyhemoglobin intersect (for example, $\lambda 1 < 805$ nm and $\lambda 2 > 805$ nm). That is, the laser beam B1 is a "first light beam" in the present invention, having a center wavelength of a wavelength region in which the amount of absorption of the oxyhemoglobin is larger than that of the deoxyhemoglobin and the laser beam B2 is a "second light beam" in the present invention, having a center wavelength of a wavelength region in which the amount of absorption of the deoxyhemoglobin is larger than that of the oxyhemoglobin. In such a case, it is preferable that the wavelengths $\lambda 1$ and $\lambda 2$ be wavelengths in which a difference between the absorption coefficient of the oxyhemoglobin and the absorption coefficient of the deoxyhemoglobin in each of the light beams B1 and B2 becomes larger.

The broad-band light sources 2A and 2B correspond to "a plurality of light sources" in the present invention and each are composed of an SLD, a light emitting diode (LED), or the like. Note that a coherent length of an available near-infrared region SLD is about 30 μm and a coherent length of a LED is about 10 μm.

The light beam emitting portion 2 further includes a beam splitter 2C and a reflecting mirror 2D. The beam splitter 2C is composed of, for example, a half mirror obliquely provided on an optical path of the light beam B1 from the broad-band light source 2A. The reflecting mirror 2D is composed of a total reflection mirror obliquely provided on an optical path of the light beam B2 from the broad-band light source 2B. The light beam B2 reflected on the reflecting mirror 2D is incident on the beam splitter 2C. Although described in detail later, the control is performed so as to alternately emit the light beams B1 and. B2. Therefore, the light beam B outputted from the light beam emitting portion 2 at an arbitrary instant is any one of the light beams B1 and B2.

In an xyz-coordinate system shown in FIG. 1, a propagating direction of the light beam B outputted from the light beam emitting portion 2 is defined as a z-axis direction and an oscillation plane of the light beam B orthogonal to the propagating direction thereof is defined as an xy-plane. An x-axis direction and a y-axis direction are defined so as to align with an oscillation plate of an electric field component of the light beam B and an oscillation plate of a magnetic field component thereof, respectively.

The polarizing plate 3 corresponds to "first converting means" in the present invention and is a polarization conversion element for transmitting an oscillation component of the light beam B in a predetermined direction, which is outputted from the light beam emitting portion 2. In this embodiment, the polarizing plate 3 is constructed to transmit an oscillation component in an angle direction of 45° relative to an x-axis (and a y-axis) of the xy-plane. The light beam B passing through the polarizing plate 3 has linearly polarized light of 45°. Therefore, the amplitudes of polarization components of the light beam B in the x-axis direction and the y-axis direction are equal to each other. In other words, the amplitude of a P-polarized light component of the light beam B is equal to that of an S-polarized light component thereof.

The half mirror 6 composes "dividing means" in present invention, for dividing the light beam B of linear polarization which is converted to the parallel light beam into the signal light S propagating to the object to be measured O and the reference light R propagating to the reference mirror 9. The half mirror 6 transmits a part (half) of the light beam B as the signal light S and reflects the rest thereof as the reference light R.

The half mirror 6 composes "super imposing means" in the present invention and has a function of reflecting a part of the signal light S propagating through the object to be measured O and transmitting a part of the reference light R propagating through the reference mirror 9 to superimpose the signal light S and the reference light R on each other, thereby producing the interference light L.

In this embodiment, because a Michelson interferometer which is composed of the object to be measured O and the reference mirror 9 which serve as reflectors and the half mirror 6 is used, the dividing means and the superimposing means are composed of (different reflective surface of) the same half mirror 6. On the other hand, when another interferometer such as a Mach-Zehnder interferometer is employed, an optical element composing the dividing means may be different from that composing the superimposing means. An arbitrary non-polarization beam splitter having no effect on the polarization characteristics of the light beam B, the signal light S, and the reference light R is applied to each of the dividing means and the superimposing means.

A ½-wavelength plate for phase correction may be disposed on the optical path of the signal light S (optical path between the half mirror 6 and the object to be measured O). In particular, it is desirable that the polarizing plate be provided on the optical path of the signal light S to locate the polarization axis in the angle direction of 45°. Therefore, even in the case where the polarization direction of the signal light S is changed by a phase difference caused when the signal light S passes through the object to be measured O and thus a ratio between an S-polarized light component L1 of the interference light L and a P-polarized light component L2 thereof which are described later changes, efficient measurement can be performed by the rotation of the polarization axis of the signal light S (particularly, in the angle direction of 45°) by the ½-wavelength plate.

The wavelength plate 7 composes "second converting means" in the present invention and is a polarization conversion element for converting the polarization characteristic of the reference light R from linear polarization to circular polarization. In this embodiment, a ⅛-wavelength plate is used as the wavelength plate 7. Therefore, when the reference light R passes through the wavelength plate 7, a phase difference of $\pi/4$ is provided between a P-polarized light component of the reference light R and an S-polarized light component thereof. In each of the case where the reference light R propagates from the half mirror 6 to the reference mirror 9 and the case where the reference light R is reflected on the reference mirror 9 and incident on the half mirror 6 again, the above-mentioned phase difference is applied to the reference light R. As a result, a phase difference of $\pi/2$ is applied to the reference light R. Thus, the wavelength plate 7 acts on the reference light R having linearly polarized light of 45° in the same manner as the ¼-wavelength plate, so the reference light R which is incident on the half mirror 6 again is converted to circularly polarized light. When another interferometer such as the Mach-Zehnder interferometer is used as described above, it is possible to apply the ¼-wavelength plate.

The frequency shifter 8 composes "frequency shifting means" in the present invention and shifts a frequency of the reference light R before and after it is reflected on the reference mirror 9. The frequency shifter 8 is composed of, for example, an optoelectronic modulator or an acoustooptic modulator. Note that it is also possible to remove the frequency shifter 8 from the optical image measuring apparatus according to the present invention. In such a case, the frequency of the reference light R is shifted by moving the reference mirror 9 (z-scanning).

The reference mirror 9 composes a "reference object" in the present invention and is moved in an optical path direction of the reference light R to extract reflection light of the signal light S at each depth (z-coordinate) of the object to be measured O. More specifically, because the light beam B from the light beam emitting portion 2 is the low-coherent light, only the signal light S propagating a distance substantially equal to a propagating distance of the reference light R is useful to produce the interference light L. In other words, only reflection light on the object to be measured O at a z-position which is located at a distance substantially equal to a distance to the reference mirror 9 relative to the half mirror 6 interferes with the reference light R to produce the interference light L. Therefore, the position of the reference mirror 9 is changed (z-scanning is performed) to continuously extract reflection light on a region of the object to be measured at O at each z-coordinate, that is, each depth.

The reference mirror 9 is moved in the optical path direction of the reference light R by the piezoelectric element 9A to scan the object to be measured O in the depth direction thereof as described above. When the reference mirror 9 is continuously moved, the frequency of the reference light R is shifted. Frequency shift applied by the movement of the reference mirror 9 may be referred to as Doppler frequency shift. At this time, the reference mirror 9 and the piezoelectric element 9A compose "frequency shifting means" in the present invention.

The optical image measuring apparatus 1 further includes an imaging lens group 10 for imaging the interference light L produced by the half mirror 6 serving as the superimposing means, a polarization beam splitter 11 for dividing an optical path of the interference light L into two based on the polarization characteristics thereof, and CCDs (cameras) 21 and 22 provided on respective optical paths into which the optical path of the interference light L is divided. Respective results obtained by detection with the CCD 21 and 22 are transmitted to a signal processing portion 20.

The polarization beam splitter 11 composes "extracting means" in the present invention, for extracting a plurality of different polarized light components from the interference light L. More specifically, the polarization beam splitter 11 acts to reflect the S-polarized light component L1 of the interference light L to allow the reflected S-polarized light component L1 to enter the CCD 21 and to transmit the P-polarized light component L2 thereof to allow the transmitted P-polarized light component L2 to enter the CCD 22. The amplitude (that is, maximum intensity) of the S-polarized light component L1 of the interference light L is equal to that of the P-polarized light component L2 thereof.

The CCDs 21 and 22 compose "(two-dimensional) detecting means" in the present invention and each are a storage type two-dimensional photo sensor array for interference light detection which has a two-dimensional light receiving surface. The CCD 21 detects the S-polarized light component L1 of the interference light L which is reflected on the polarization beam splitter 11, performs photoelectric conversion to generate a detection signal, and outputs the detection signal to the signal processing portion 20. Similarly, the CCD 22 detects P-polarized light component L2 of the interference light L which passes through the polarization beam splitter 11, performs photoelectric conversion to generate a detection signal, and outputs the detection signal to the signal processing portion 20. Each of the detection signals outputted from the CCDs 21 and 22 is the above-mentioned heterodyne signal.

The signal processing portion 20 executes calculation processing described later based on the detection signals outputted from the CCDs 21 and 22. The signal processing portion 20 analyzes a result obtained by the calculation processing to form various images such as two-dimensional and three-dimensional tomographic images of the object to be measured O and causes a display device such as a monitor device (see FIG. 3) to display the images. The signal processing portion 20 is composed of, for example, a computer which includes a storage device storing a predetermined calculation program, such as a ROM, and a calculation control device executing the calculation program, such as a CPU. The signal processing portion 20 is "image forming means" in the present invention.

The optical image measuring apparatus 1 further includes a light source 31, a beam splitter 32, a reflecting mirror 33, a photo detector (PD) 34, and a light source driving portion 35, which compose a structure for monitoring the amount of frequency shift applied to the reference light R and periodically modulate the light beam B from the light beam emitting portion 2 based on the monitored amount of frequency shift.

The light source 31 is composed of, for example, a laser diode for emitting laser light having a coherent length longer than that of the light beam from the light beam emitting portion 2. The beam splitter 32 divides the laser light from the light source 31 into first laser light (reflection light) propagating through the frequency shifter 8 and the reference mirror 9 and second laser light (transmission light) propagating through the reflecting mirror 33 which is fixedly disposed. Then, the beam splitter 32 superimposes the first laser light which has been subjected to frequency shift by the frequency shifter 8 or the like and the second laser light reflected on the reflecting mirror 33 on each other to produce interference light (referred to as assistant interference light).

The photo detector 34 detects the assistant interference light and outputs an electrical signal having a frequency equal to a beat frequency of the assistant interference light to the light source driving portion 35. The beat frequency of the assistant interference light is equal to the amount of frequency shift applied to the reference light R, so the beat frequency of the assistant interference light becomes equal to the beat frequency of the interference light L.

The light source driving portion 35 composes "light source driving means" in the present invention and generates a pulse signal having a frequency equal to that of the electrical signal outputted from the photo detector 34. Then, the light source driving portion 35 processes the pulse signal to form light source drive signals for separately driving the respective broad-band light sources 2A and 2B.

Although described in detail later, each of the light source drive signals includes a frequency component equal to a frequency of the pulse signal, that is, the beat frequency of the interference light L and a frequency component synchronized with a time interval (frame interval or frame rate) for detection with each of the CCDs 21 and 22. The former frequency component corresponds to a frequency for intensity modulation of the outputted light beams B1 and B2 (referred to as an intensity modulation frequency component) The latter frequency component is used to synchronize a switching period for alternately switching between the light beams B1 and B2 to be outputted with the time interval for detection with each of the CCDs 21 and 22, that is, to synchronize a switching frequency between the light beams B1 and B2 with the frame rate for each of the CCDs 21 and 22 (referred to as a wavelength switching frequency component).

The light source drive signals are outputted to the respective broad-band light sources 2A and 2B. A phase difference based on a detection interval for each of the CCDs 21 and 22 (frame interval; a predetermined time interval in the present invention) is provided between the light source drive signals outputted to the broad-band light sources 2A and 2B.

The light beam emitting portion 2 is driven based on the drive signals outputted from the light source driving portion 35. The intensities of the light beams B1 and B2 to be alternately outputted are modulated at a frequency equal to the intensity modulation frequency component while switching between the light beams B1 and B2 at a frequency equal to the wavelength switching frequency component.

The light beam emitting portion 2 and the light source driving portion 35 compose "light beam outputting means" in the present invention.

[Structure of Control System]

Next, the control system of the optical image measuring apparatus 1 will be described with reference to FIGS. 3 and 4.

As shown in FIG. 3, the control system of the optical image measuring apparatus 1 includes the light source driving portion 35 for driving the broad-band light sources 2A and 2B, a display device 36 for displaying the images formed by the signal processing portion 20, and a control portion 37 for controlling respective portions of the apparatus.

(Control Portion)

The detection signal from the photo detector 34, the images (image data) formed by the signal processing portion 20, and the like are inputted to the control portion 37. The control portion 37 sets the time interval for detection with each of the CCDs 21 and 22 (that is, the frame interval or the frame rate). The frame rates for the respective CCDs 21 and 22 are set so as to be equal to each other (for example, 30 frames per second). Although are substantially identical with the frame rates, the frame interval may be set (for example, 30 milliseconds per frame). When the frame rate (frame interval) for the CCDs 21 and 22 is maintained constant, the frame rate (frame interval) value is stored in the control portion 37 (or stored in a memory or the like which can be accessed by the control portion 37). The control portion 37 controls a piezoelectric drive portion (not shown) for driving the piezoelectric element 9A to shift the position of the reference mirror 9.

(Light Source Driving Portion)

Figure 4A:

The light source driving portion 35 generates the above-mentioned light source drive signals for separately driving the broad-band light sources 2A and 2B under the control of the control portion 37. Therefore, the light source driving portion 35 firstly generates a pulse signal (first pulse signal) which has a frequency synchronized with the electrical signal outputted from the photo detector 34 (for example, a frequency equal to that of the electrical signal). The first pulse signal corresponds to the above-mentioned intensity modulation frequency component. FIG. 4A is a schematic diagram showing the first pulse signal.

Figure 4B:
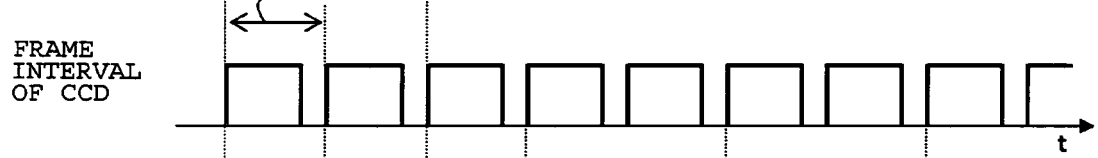
Figure 4C:
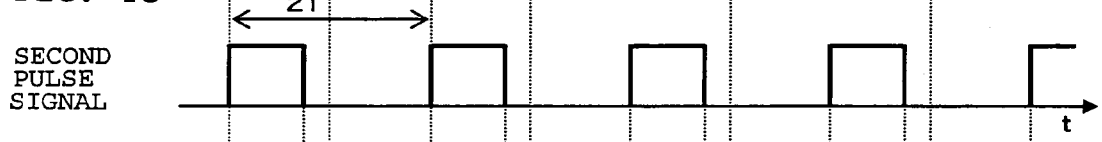

The light source driving portion 35 generates a pulse signal (second pulse signal) which has a frequency synchronized with the frame rate based on set value information of the frame rate (or the frame interval; same as above) for the CCDs 21 and 22 which is set by the control portion 37. The second pulse signal corresponds to the above-mentioned wavelength switching frequency component. FIG. 4B illustrates a detection timing for the CCDs 21 and 22 in time-series, in which the frame interval is set to T (seconds). FIG. 4C is a schematic diagram showing a signal having a frequency equal to two times the frame interval for the CCDs 21 and 22, that is, ½ of the frame rate, as an example of the second pulse signal.

Figure 4D:

The light source driving portion 35 forms a composite (multiplied) signal from the first pulse signal and the second pulse signal. FIG. 4D is a schematic diagram showing the composite signal. The composite signal is produced by extracting only pulses corresponding to pulse portions of the second pulse signal from respective pulses of the first pulse signal. The composite signal is used as the first light source drive signal for driving the broad-band light source 2A.

Figure 4E:

The light source driving portion 35 generates a signal in which the phase of the formed first light source drive signal is shifted by the amount of shift corresponding to the frame interval for the CCDs 21 and 22 (see FIG. 4E). The signal is used as a second light source drive signal for driving the broad-band light source 2B.

The light source driving portion 35 outputs the first light source drive signal and the second light source drive signal which are obtained as described above to the broad-band light source 2A of the light beam emitting portion 2 and the broad-band light source 2B thereof, respectively.

(Display Device)

The display device 36 is composed of a monitor device such as a liquid crystal display or a CRT display and displays an image based on an image signal outputted from the control portion 37.

(Signal Processing Portion)

The signal processing portion 20 includes a calculation portion 20A (calculating means) for calculating the signal intensity of the interference light L and the phase thereof based on results obtained by detection with the CCDs 21 and 22 and an image forming portion 20B for forming, for example, a tomographic image of the object to be measured O based on a result obtained by calculation in the calculation portion 20A. Processings executed by the calculation portion 20A and the image forming portion 20B will be described later.

[Measurement Mode]

Subsequently, measurement processing on the spatial signal intensity distribution of the interference light L and the spatial phase distribution thereof and image forming processing on the object to be measured O, which are executed by the optical image measuring apparatus 1 according to this embodiment will be described. The following detailed signal processing is executed by the signal processing portion 20 shown in FIGS. 1 and 3.

The optical image measuring apparatus 1 forms the signal light S and the reference light R whose polarization characteristics are different from each other and detects the interference light L of those as the heterodyne signal to obtain a surface image or a tomographic image of the object to be measured O.

[Measurement Principle]

First, the basic principle of measurement executed by the optical image measuring apparatus 1 will be described. The light beam outputted from the light beam emitting portion 2 is converted to the linearly polarized light in the angle direction of 45° relative to the x-axis by the polarizing plate 3. The beam diameter of the converted linearly polarized light is increased by the lenses 4 and 5 and the linearly polarized light whose beam diameter is increased is converted to the parallel light beam thereby. Then, the light beam is incident on the half mirror 6 and divided into two, that is, the signal light S and the reference light R.

The signal light S is incident on the object to be measured O, which is made of a scattering medium, and reflected on a surface thereof and sectional surfaces at various depths. A part of a reflection light wave from the object to be measured O is reflected on the half mirror 6 and propagates to the imaging lens group 10.

On the other hand, the reference light R passes through the wavelength plate 7 and propagates to the reference mirror 9. At this time, the reference mirror 9 is driven (z-scanning is performed) in the optical direction of the reference light R by the piezoelectric element 9A. The reference light R is subjected to frequency shift having a predetermined amount by the frequency shifter 8. A reflection light wave on the reference mirror 9 is subjected to Doppler frequency shift by the z-scanning of the reference mirror 9 and further subjected to frequency shift by the frequency shifter 8, and then passes through the wavelength plate 7. Here, because the polarization characteristic of the reference light R is the linear polarization of 45° and the wavelength plate 7 is the ⅛-wavelength plate, the polarization characteristic of the reference light R passing through the wavelength plate 7 two times is converted to the circular polarization. A part of the reference light R whose polarization characteristic is converted to the circular polarization passes through the half mirror 6 and propagates to the imaging lens group 10.

At this time, the half mirror 6 superimposes the signal light S of the linear polarization which is reflected on the object to be measured O and the reference light R whose frequency is shifted and polarization characteristic is converted to the circular polarization on each other to produce the interference light L. The interference light L propagates to the polarization beam splitter 11 through the imaging lens group 10.

The polarization beam splitter 11 acts to reflect the S-polarized light component L1 of the interference light L and to transmit the P-polarized light component L2 thereof. The S-polarized light component L1 of the interference light L is detected by the CCD 21 and the P-polarized light component L2 thereof is detected by the CCD 22. The S-polarized light component L1 of the interference light L includes an S-polarized light component Ess of the signal light S and an S-polarized light component Ers of the reference light R. The P-polarized light component L2 of the interference light L includes a P-polarized light component Esp of the signal light S and a P-polarized light component Erp of the reference light R. The S-polarized light component Ess of the signal light S, the P-polarized light component Esp thereof, the S-polarized light component Ers of the reference light R, and the P-polarized light component Erp thereof each are expressed by the following expressions.

$$Ess = \sqrt{I_{ss}}\sin(2\pi ft + \phi) \quad (2)$$

$$Esp = \sqrt{I_{sp}}\sin(2\pi ft + \phi) \quad (3)$$

$$Ers = \sqrt{I_{rs}}\sin[2\pi(f+f_D)t + \phi'] \quad (4)$$

$$Erp = \sqrt{I_{rp}}\sin[2\pi(f+f_D)t + \phi' + 90°] \quad (5)$$

Here, f indicates a frequency of the light beam outputted from the light beam emitting portion 2, $f_D$ indicates a frequency shift, $\Phi$ indicates an initial phase of the signal light S, and $\Phi'$ indicates an initial phase of the reference light R. Assume that a difference between the initial phase of the signal light S and the initial phase of the reference light R is given by $\Delta\Phi(=\Phi-\Phi')$. Referring to the expressions (2) to (5), the S-polarized light component L1 of the interference light L and the P-polarized light component L2 thereof are detected by the CCDs 21 and 22 as heterodyne signals $i_1$ and $i_2$ expressed by the following expressions.

$$i_1 \propto |E_{ss}+E_{rs}|^2 \propto I_{rs}+I_{ss}+2\sqrt{I_{rs}I_{ss}}\cos(2\pi f_D t + \Delta\phi) \quad (6)$$

$$i_2 \propto |E_{sp}+E_{rp}|^2 \propto I_{rp}+I_{sp}+2\sqrt{I_{rp}I_{sp}}\sin(2\pi f_D t + \Delta\phi) \quad (7)$$

As is apparent from the comparison between the expressions (6) and (7), a phase difference between the alternating signals of the third terms of the respective expressions is 90° because of the cosine and sine functions with the same phase. In the optical image measuring apparatus 1, in addition to utilizing such a feature, the light beams whose intensity is periodically modulated is used as measurement light to allow the realization of optical heterodyne detection without sampling processing using shutters, thereby measuring the signal intensity of the interference light L and the spatial phase distribution thereof. In a conventional optical image measuring technique, single interference light is sampled using a plurality of functions having different phases to detect cosine and sine components thereof. In contrast to this, the feature of the present invention is that the polarization characteristics of the reference light R and the signal light S are converted to produce the plurality of (two in this embodiment) interference light components having the different phases and the produced interference light components are separately detected. Hereinafter, measurement fundamentals in the present invention will be described.

In the optical image measuring apparatus 1, the light beam whose intensity is modulated at the frequency synchronized with the beat frequency of the interference light L is outputted from the light beam emitting portion 2 by using the light source 31, the beam splitter 32, the reflecting mirror 33, the photo detector (PD) 34, and the light source driving portion 35.

The laser light outputted from the light source 31 is divided by the beam splitter 32 into an optical path in the reference mirror 9 direction (reflection light) and an optical path in the reflecting mirror 33 direction (transmission light). The laser light beam on the optical path in the reference mirror 9 direction is subjected to frequency shift by the frequency shifter 8 and the reference mirror 9 while the laser light beam propagates therethrough, and then is incident on the beam splitter 32 again. On the other hand, the laser light beam on the optical path in the reflecting mirror 33 direction is incident, as reflection light on the reflecting mirror 33, on the beam splitter 32 again (without frequency shift). The laser light beams propagating on both the optical paths are superimposed on each other by the beam splitter 32 to produce assistant interference light. The assistant interference light is detected by the photo detector 34.

As in the case of the reference light R, the assistant interference light detected by the photo detector 34 is subjected to the frequency shift using the frequency shifter 8 and the Doppler frequency shift using the reference mirror 9. Therefore, the assistant interference light is subjected to frequency shift having the amount of shift (substantially) equal to that of the reference light R. Thus, the assistant interference light has a beat frequency (substantially) equal to that of the interference light L produced from the signal light S and the reference light R.

The photo detector 34 outputs an electrical signal corresponding to the detected assistant interference light to the light source driving portion 35. As in the case of the heterodyne signal expressed by the expression (1), the electrical signal includes a direct current component and an alternating current component. The alternating current component has a frequency substantially equal to the beat frequency of the interference light L as described above.

As described above with reference to FIGS. 4A to 4E, the light source driving portion 35 generates the first light source drive signal and the second light source drive signal based on the electrical signal from the photo detector 34 and outputs the generated first and second light source drive signals to the light beam emitting portion 2. The broad-band light source 2A of the light beam emitting portion 2 is driven based on the first light source drive signal and outputs the pulsed light beam B1 having the wavelength λ1. The broad-band light source 2B is driven based on the second light source drive signal and outputs the pulsed light beam B2 having the wavelength λ2.

As is apparent from the phase difference between the first and second light source drive signals shown in FIGS. 4D and 4E, the light beam B1 and the light beam B2 are alternately outputted by switching. The switching frequency is synchronized with (equal to in this embodiment) the frame rate for the CCDs 21 and 22. Therefore, each of the CCDs 21 and 22 alternately detects the interference light L resulting from the light beam B1 and the interference light L resulting from the light beam B2 for each frame. The intensity of each of the light beams B1 and B2 is modulated at the frequency synchronized with the beat frequency of the interference light L (output ON/OFF switching is performed in this embodiment).

The output intensity of each of the light beams B1 and B2 may be modulated not between 0 and 100 but between, for example, 50 and 100. That is, the important point is not to control the degree of the intensity modulation of each of the light beams B1 and B2 but to control the frequency for the intensity modulation such that the frequency therefor becomes substantially equal to the beat frequency of the interference light L.

Next, a detection mode of the interference light L in the optical image measuring apparatus 1 according to this embodiment will be described with reference to graphs shown in FIGS. 5A to 5E. Hereinafter, assume that a modulation frequency of the intensity of the light beam B (light beam B1/B2, refer to FIG. 2) outputted from the light beam emitting portion 2 is $f_m$. As described above, $f_D$ indicates the frequency shift applied to the reference light R (beat frequency of the interference light L). Assume that the modulation frequency $f_m$ of the light beam is equal to or closer to the frequency shift $f_D$.

FIG. 5A illustrates a time waveform of the light beam B which is subjected to intensity modulation at the frequency $f_m$ and outputted from the light beam emitting portion 2. FIG. 5B illustrates a time waveform of the S-polarized light component L1 of the interference light L (beat frequency $f_D$) in the case where the light beam B is continuous light and thus the reference light R and the signal light S each are continuous light. FIG. 5C illustrates a time waveform of the P-polarized light component L2 of the interference light L in the case where the reference light R and the signal light S each are continuous light. A phase difference between the S-polarized light component L1 and the P-polarized light component L2 can be arbitrarily set. The phase difference shown in FIGS. 5B and 5C is set to 90°.

FIG. 5D illustrates a time waveform of the S-polarized light component L1 of the interference light L in the case where the light beam B from the light beam emitting portion 2 is subjected to the intensity modulation as shown in FIG. 5A (this corresponds to FIG. 5B). FIG. 5E illustrates a time waveform of the P-polarized light component L2 of the interference light L in the case where the light beam B is subjected to the intensity modulation as shown in FIG. 5A (this corresponds to FIG. 5C). A phase difference between the S-polarized light component L1 and the P-polarized light component L2 as shown in FIGS. 5D and 5E is 90°.

The CCD 21 detects the S-polarized light component L1 having the time waveform shown in FIG. 5D. The light beam B from the light beam emitting portion 2 is a light pulse having the modulation frequency $f_m$. When a difference between the modulation frequency $f_m$ and the beat frequency $f_D$ of the interference light L ($\delta f=|f_m-f_D|$) is sufficiently smaller than a response frequency of the CCD 21 serving as the storage type photo sensor, a detection signal of the S-polarized light component L1 which is outputted from the CCD 21 becomes proportional to the amount of photo charge stored for a detection period. Therefore, the detection signal is expressed by the following expression (for example, see M. Akiba, K. P. Chan, and N. Tanno, Japanese Journal of Applied Physics, Vol. 39, L1194 (2000)).

$$S_1(t) = \langle K_1 m(t) i_1(t) \rangle \quad (8)$$

$$= K_1 \left[ \frac{1}{2} I_{ss} + \frac{1}{2} I_{rs} + \frac{2}{\pi} \sqrt{I_{ss} I_{rs}} \cos(2\pi \delta f t + \beta) \right]$$

Here, <•> indicates a time average produced by a storage effect of the CCD 21. In addition, $K_1$ indicates photo detection efficiency including reflectance of the polarization beam splitter 11 and a photoelectric conversion rate of the CCD 21, m(t) indicates a function for modulating the output intensity of the broad-band light source 2 (function indicating a rectangular pulse), and β indicates an initial phase value for measurement. As is apparent from the expression (8), the detection signal outputted from the CCD 21 includes the term related to an amplitude $\sqrt{(I_{ss} I_{rs})}$ of the S-polarized light component L1 of the interference light L and a phase ($2\pi\delta ft+\beta$) thereof in addition to the term related to the intensity of the signal light S and the term related to the intensity of the reference light R (background light component).

Similarly, the CCD 22 detects the P-polarized light component L2 having the time waveform shown in FIG. 5E and outputs a detection signal as expressed by the following expression.

$$S_2(t) = K_2 \left[ \frac{1}{2} I_{sp} + \frac{1}{2} I_{rp} + \frac{2}{\pi} \sqrt{I_{sp} I_{rp}} \sin(2\pi \delta f t + \beta) \right] \quad (9)$$

Here, $K_2$ indicates photo detection efficiency including transmittance of the polarization beam splitter 11 and a photoelectric conversion rate of the CCD 22.

Next, calculation processing of the signal intensity of the interference light L based on the detection signals (expressed by the expressions (8) and (9)) outputted from the CCDs 21 and 22 will be described.

Because the reference light R is converted to the circularly polarized light by the wavelength plate 7, it can be considered that an intensity $I_{rs}$ of the S-polarized light component Ers of the reference light R is equal to an intensity $I_{rp}$ of the P-polarized light component Erp thereof (this indicates $I_{rs}=I_{rp}=I_r$).

On the other hand, it is assumed that the reflection light of the signal light S on the object to be measured O does not significantly depend on the polarization characteristic of the incident light thereof, so it can be considered that an intensity $I_{SS}$ of the S-polarized light component Ess of the signal light S is equal to or close to the intensity $I_{sp}$ of the P-polarized light component Esp thereof (this indicates $I_{ss}=I_{sp}=I_s$). Because the signal light S is scattered or absorbed in the object to be measured O, it can be assumed that the intensity thereof is generally sufficiently smaller than that of the reference light R ($I_s<<I_r$).

The first term and the second term of the right side of each of the expressions (8) and (9) indicate the intensity of the background light. The intensity of the background light can be measured in advance or separately. For example, a light beam which is continuous wave light is outputted from the broad-band light source 2 and detected by the CCD 21 and the like. The detected light beam is integrated for a period corresponding to one wavelength (or integral multiple thereof) and the third term (alternating current component; phase quadrature component) is cancelled. Therefore, it is possible to obtain the intensity of the background light (background light component).

The obtained background light component is divided by the intensities of the detection signals from the CCDs 21 and 22 to calculate phase quadrature components of the detection signals, that is, a phase quadrature component $S_1'(t)$ of the S-polarized light component L1 of the interference light L and a phase quadrature component $S_2'(t)$ of the P-polarized light component L2 thereof (see the following expressions).

$$S_1'(t) = K_1 \frac{2}{\pi} \sqrt{I_s I_r} \cos(2\pi \delta f t + \beta) \quad (10)$$

$$S_2'(t) = K_2 \frac{2}{\pi} \sqrt{I_s I_r} \sin(2\pi \delta f t + \beta) \quad (11)$$

When the expressions (10) and (11) are used, the amplitude of the S-polarized light component L1 of the interference light L and the amplitude of the P-polarized light component L2 thereof are expressed by the following expression.

$$\sqrt{I_s I_r} \propto \sqrt{S_1'^2 + S_s'^2} \quad (12)$$

The optical image measuring apparatus 1 according to this embodiment produces an image of a spatial phase distribution of the interference light L as follows.

Assume that, at a measurement time $t=t_1$, a phase quadrature component $S_1'(t_1)$ of the S-polarized light component L1 of the interference light L is detected by the CCD 21 and a phase quadrature component $S_2'(t_1)$ of the P-polarized light component L2 thereof is detected by the CCD 22. When a ratio between both the phase quadrature components is calculated, the following signal is obtained.

$$S_3 = \frac{S_2'(t_1)}{S_1'(t_1)} = \tan(2\pi \delta f t_1 + \beta) \quad (13)$$

As is apparent from the expression (13), a signal $S_3$ expressed thereby does not depend on the amplitude of the interference light L and is composed of only phase information. In this embodiment, the S-polarized light component L1 and the P-polarized light component L2 are detected by the CCDs 21 and 22, each of which has a light receiving surface on which a plurality of pixels are two-dimensionally arranged. Therefore, a phase $\beta(x, y, t_1)$ of a signal detected from each of the pixels is expressed by the following expression (where (x, y) indicates coordinates of each of the pixels on the light receiving surface).

$$\beta(x, y, t_1) = \tan^{-1}\left[\frac{S_2'(x, y, t_1)}{S_1'(x, y, t_1)}\right] - 2\pi \delta f t_1 \quad (14)$$

The second term of the expression (14) is an instantaneous phase value of an alternating current signal having a frequency $\delta f$ of zero or substantially zero ($\approx 0$) at the measurement time $t_1$, so it can be considered that the phase value is maintained constant regardless of the positions of the pixels of the CCDs 21 and 22, that is, the coordinates (x, y) thereof. Therefore, for example, a difference between a reference phase $\Phi((x_1, y_1, t_1)$ of a detection signal detected from a pixel located at a specific point ($x=x_1, y=y_1$) on the light receiving surface of each of the CCDs 21 and 22 and a phase of a detection signal detected from each of the pixels is obtained. Thus, it is possible to image a spatial phase difference distribution of the heterodyne signals, that is, a spatial phase difference distribution of the interference light L.

The frequency information of the interference light L can be also obtained from the phase information thereof. Assume that the phases of the interference light L (S-polarized light component L1 and P-polarized light component L2) at two measurement times $t=t_1$ and $t=t_2$ are denoted by $\beta(x, y, t_1)$ and $\beta(x, y, t_2)$. Then, the difference $\delta f$ between the beat frequency $f_D$ of the interference light L and the modulation frequency $f_m$ of the light beam from the light beam emitting portion 2 is expressed by the following expression.

$$\delta f = \frac{1}{2\pi}\left|\frac{\beta(x, y, t_1) - \beta(x, y, t_2)}{t_1 - t_2}\right| \quad (15)$$

Because the modulation frequency $f_m$ of the light beam is known, the heterodyne frequency, that is, the beat frequency $f_D$ of the interference light L can be calculated based on the expression (10) or (11).

[Imaging of Functional Information on Living Tissue]

A measurement mode in the present invention, that is, processing for forming an image including functional information on a living tissue, which is executed based on the measurement principle of the optical image measuring apparatus 1 will be described. The following calculation processing is executed by the calculation portion 20A of the signal processing portion 20 and image forming processing based on a result obtained by the calculation processing is executed by the image forming portion 20B. Hereinafter, the oxygen saturation of hemoglobin is considered as an example of the functional information on the living tissue.

As described above, the optical image measuring apparatus 1 alternately outputs the light beam B1 having the wavelength $\lambda 1$ and the light beam B2 having the wavelength $\lambda 2$ at the frequency synchronized with the frame rate for the CCDs 21 and 22. Note that each of the wavelengths $\lambda 1$ and $\lambda 2$ is set to the vicinity of a frequency at which the absorption characteristic of the oxyhemoglobin and the absorption characteristic of the deoxyhemoglobin intersect. In this embodiment, the wavelength $\lambda 1$ of the light beam B1 is set to a wavelength at which the light beam B1 is more absorbed by the oxyhemoglobin (for example, 840 nm). In addition, the wavelength $\lambda 2$ of the light beam B2 is set to a wavelength at which the light beam B2 is more absorbed by the deoxyhemoglobin (for example, 760 nm).

Assume that the maximum intensities of the light beams B1 and B2 are equal to each other. At this time, assume that an intensity of the signal light S incident on the object to be measured (living tissue) O is expressed by $I_{in}$. In addition, assume that a scattering and absorption coefficient of the object to be measured O is expressed by $\sigma = \sigma(\lambda)$ and a depth at which the signal light S interfering with the reference light R is reflected in the object to be measured O (that is, half of the distance which the signal light S involved in producing the interference light L propagates through the object to be measured O) is expressed by l. At this time, an intensity $I_{out,1}$ of the signal light S based on the laser beam B1 ($\lambda 2$ in wavelength), which exits from the object to be measured O and an intensity $I_{out,2}$ of the signal light S based on the laser beam B2 ($\lambda 2$ in wavelength), which exits from the object to be measured O are expressed by the following expressions.

$$I_{out,1} = I_{in} \exp\{-2\sigma(\lambda 1)l\} \quad (16)$$

$$I_{out,2} = I_{in} \exp\{-2\sigma(\lambda 2)l\} \quad (17)$$

The logarithms of both sides of the respective expressions (16) and (17) are taken and organized to derive the following expressions.

$$T_1 = \log \frac{I_{in,1}}{I_{out,1}} = 2\sigma(\lambda 1)l \qquad (18)$$

$$T_2 = \log \frac{I_{in,2}}{I_{out,2}} = 2\sigma(\lambda 2)l \qquad (19)$$

Further, the following relationship is obtained from the expressions (18) and (19).

$$(T1-T2)/2l = \sigma(\lambda 1) - \sigma(\lambda 2) \qquad (20)$$

The right side of the expression (20) indicates a difference between a scattering and absorption coefficient σ(λ1) corresponding to the wavelength λ1 of the light beam absorbed mainly by the oxyhemoglobin and a scattering and absorption coefficient σ(λ2) corresponding to the wavelength λ2 of the light beam absorbed mainly by the deoxyhemoglobin. The differential value corresponds to the oxygen saturation of hemoglobin. Therefore, the values in the expression (20) are calculated over the beam cross section of the interference light L, that is, the values are calculated based on results obtained by detection from respective pixels of the CCDs 21 and 22. Thus, it is possible to form an image showing a distribution state of the oxygen saturation in a corresponding measurement region (which is an xy-region irradiated with the signal light S and a region of z-coordinate=l) of the object to be measured O.

Therefore, in view of the expressions (16) to (20), it is apparent that it is only necessary to obtain the intensity $I_{in}$ of the signal light S incident on the object to be measured O, the intensity $I_{out,1}$ of the signal light S based on the laser beam B1, which exits from the object to be measured O, the intensity $I_{out,2}$ of the signal light S based on the laser beam B2, which exits from the object to be measured O, and the depth l at which the signal light S involved in producing the interference light L is reflected in the object to be measured O.

First, the intensity $I_{in}$ of the signal light S incident on the object to be measured O can be calculated based on the amount of light beams outputted from the broad-band light sources 2A and 2B and the transmittance of the half mirror 6. When reductions in the amount of light beams which are caused by the polarizing plate 3 and the lenses 4 and 5 cannot be neglected, the transmittances of these elements are also taken into account.

Each of the intensity $I_{out,1}$ of the signal light S based on the laser beam B1 and the intensity $I_{out,2}$ of the signal light S based on the laser beam B2, which exit from the object to be measured O, can be calculated from the S-polarized light component L1 and the P-polarized light component L2 of the interference light L which are detected by the CCDs 21 and 22.

The depth l corresponding to the reflection position of the signal light S can be easily calculated from the position of the reference mirror 9. For example, when the position of the reference mirror 9 when a distance between the half mirror 6 and the reference mirror 9 and a distance between the half mirror 6 and the object to be measured O are equal to each other is set as a reference position, the depth l corresponding to the reflection position of the signal light S is obtained as the amount of displacement of the reference mirror 9 from the reference position at the time of measurement. As described above, the movement of the reference mirror 9 is controlled by the control portion 37. Therefore, the calculation portion 20A can calculate the depth l based on the positional information of the reference mirror 9 which is grasped by the control portion 37.

Thus, the optical image measuring apparatus 1 can form an image showing the distribution of the scattering and absorption coefficient in the object to be measured (living tissue) O. The distribution image of the scattering and absorption coefficient shows the distribution state of the oxygen saturation of hemoglobin in the object to be measured O.

[Operation and Effect]

As described above, according to the optical image measuring apparatus 1 in this embodiment, the two-dimensional image of the object to be measured O at a depth thereof can be obtained without scanning the object to be measured O with the signal light S. In addition, the three-dimensional image of the object to be measured O can be obtained only by the z-scanning of the reference mirror 9. Therefore, it is possible to efficiently form an image expressing the oxygen saturation of hemoglobin.

When the wavelengths λ1 and λ2 of the light beams B1 and B2 alternately outputted by switching are arbitrarily set for any purpose, an image expressing other functional information of the living tissue can be efficiently obtained.

[Modified Examples]

A method of alternately operating the broad-band light sources 2A and 2B is not limited to a method of pulse-driving the light beam emitting portion 2 by the light source driving portion 35. For example, in order to alternately output the light beams B1 and B2, light sources for emitting continuous wave light beams (continuous wave light) B1 and B2 may be used as the broad-band light sources 2A and 2B and shutters for selectively (that is, alternately) cutting off the continuous wave light beams B1 and B2 (light beam cutoff means) may be provided. In this case, the "light beam outputting means" in the present invention includes the light beam emitting portion 2 and the light beam cutoff means.

In the above-mentioned optical image measuring apparatus, both the structure using the frequency shifter 8 and the structure using the reference mirror 9 and the piezoelectric element 9A are used to apply the frequency shift to the reference light R. The apparatus may include only one of the structures. For example, even when an optical image measuring apparatus without being provided the frequency shifter 8 is produced in order to apply the frequency shift to the reference light R only by the z-scanning of the reference mirror 9, the same measurement can be executed. When the frequency shifter 8 is to be used, it may be provided on the optical path of the signal light S. This is because it is sufficient that the frequency of the signal light S and the frequency of the reference light R at the time of superimposition be shifted relative to each other in the image measurement according to the present invention.

In the above-mentioned structure, the light beam from the light beam emitting source 2 is converted to the linearly polarized light and then divided into the signal light S and the reference light R. Each of the signal light S and the reference light R may be converted to the linearly polarized light after the division of the light beam. In such a case, it is necessary to provide a polarizing plate on each of the optical path of the signal light S and the optical path of the reference light R, so such a structure becomes slightly more complex than the above-mentioned structure. Therefore, the above-mentioned structure may be more suitable in practical use.

In the above-mentioned structure, the polarization characteristic of the reference light R is converted to the circular polarization. It is also possible that the signal light S is converted to the circularly polarized light and superimposed on the reference light R which is the linearly polarized light. However, as described above, the reflection light of the signal light S which is reflected on the object to be measured O is weaker than the reference light R. Therefore, when the wavelength plate is disposed on the optical path of the signal light S, the signal light S passing therethrough weakens. The weakening of the intensity of the signal light S including information related to the object to be measured O may affect measurement sensitivity. Thus, the above-mentioned structure in which the polarization characteristic of the reference light R is converted to the circular polarization has an advantage. Note that the same is applied to the case where the frequency shifter is disposed.

In the above-mentioned structure, the light source 31, the beam splitter 32, the reflecting mirror 33, and the photo detector 34 are provided to monitor the amount of frequency shift applied to the reference light R and a monitoring result is fed back to the intensity modulation of the light beam. For example, when the amount of frequency shift applied to the reference light R is set, the light source driving portion 35 for automatically generating a pulse signal having a frequency (substantially) equal to the set amount of frequency shift may be provided to control the intensity modulation of the light beam.

The measurement mode for obtaining the tomographic image of the object to be measured O at each depth during the z-scanning of the reference mirror 9 is described. When the measurement is performed while the position of the reference mirror 9 is fixed, it is possible to obtain a still image and a dynamic picture image of the object to be measured O at a depth with high precision.

When a wavelength plate (½-wavelength plate) is provided on the optical path of the signal light S, that is, the optical path between the half mirror 6 and the object to be measured O, it is possible to correct the tilt of the signal light S in the polarization direction, which is caused by a change in phase of the signal light S passing through the object to be measured O.

The detecting means of the optical image measuring apparatus 1 are not limited to the above-mentioned CCDs. The detecting means may be a sensor having both a function of detecting the interference light and performing photoelectric conversion thereon and a function of storing detected charges, such as a line sensor including an integrating circuit. A one-dimensional sensor or a two-dimensional sensor may be used.

The optical image measuring apparatus 1 having the Michelson type interferometer is described. It is also possible to use another interferometer such as a Mach-Zehnder type interferometer or a Fizeau interferometer (for example, see JP 3245135 B made by the inventors of the present invention).

An optical fiber (bundle) used as a light guide member is provided in a part of the interferometer. Therefore, the degree of freedom of an apparatus design can be improved, the apparatus can be made compact, or the degree of freedom of location of the object to be measured can be improved (for example, see JP 3245135 B mentioned above).

Second Embodiment

Subsequently, an optical image measuring apparatus according to a second embodiment of the present invention will be described. In this embodiment, the interference light M is sampled using shutters.

[Structure of Apparatus]

Figure 6:
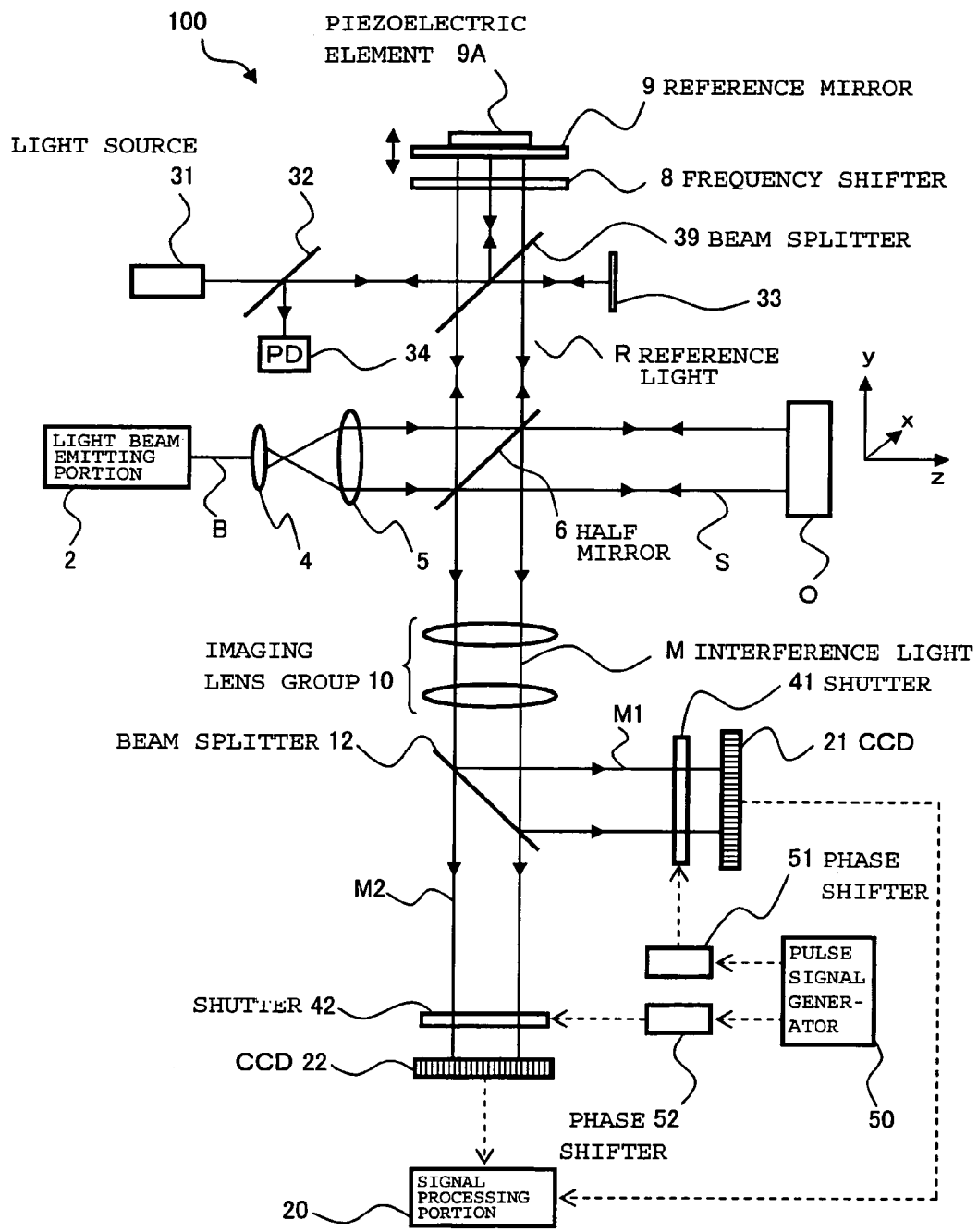
FIG. 6 is a schematic diagram showing an example of an optical system of an optical image measuring apparatus according to a second embodiment of the present invention.
Figure 7:
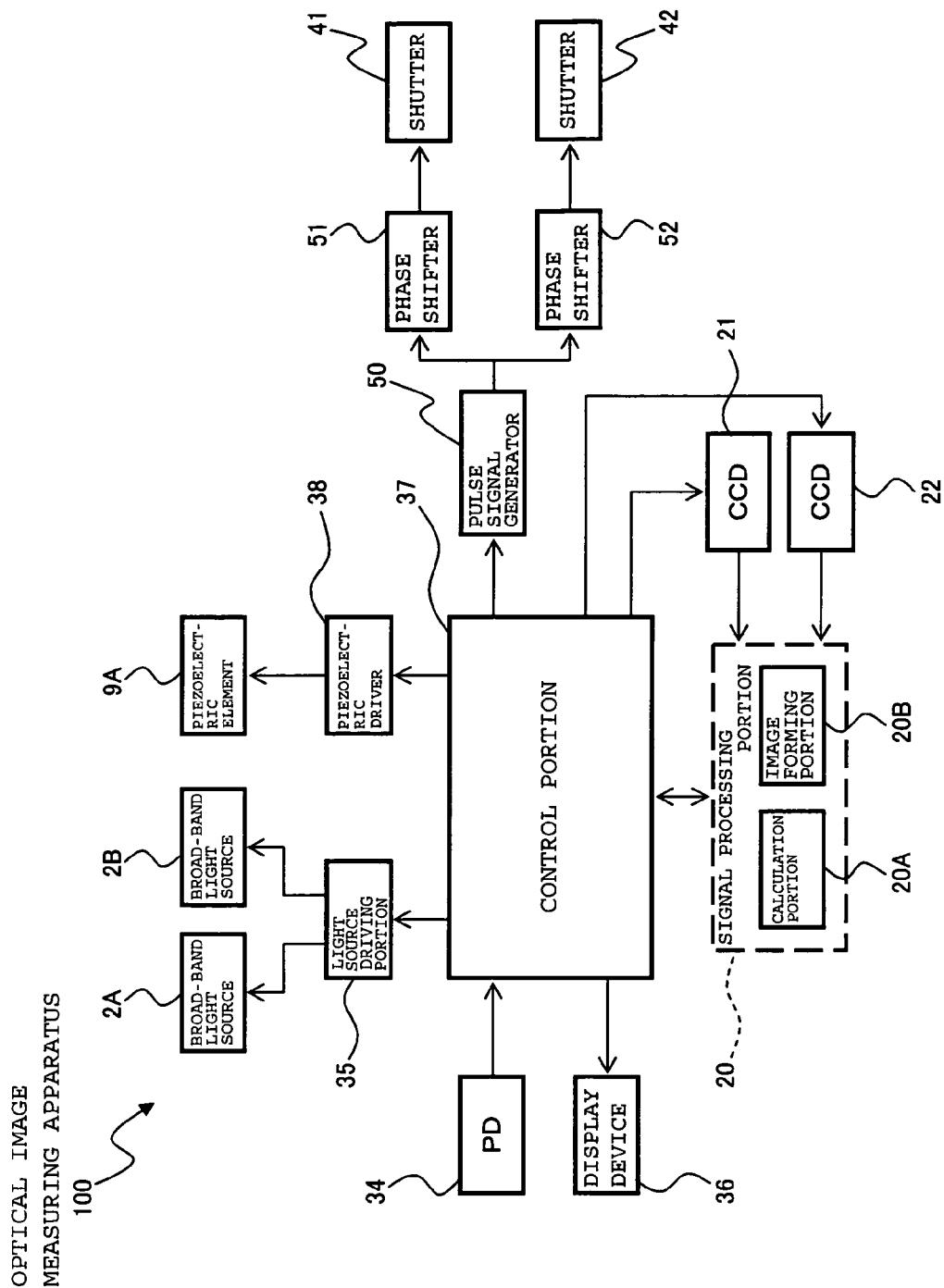
FIG. 7 is a schematic diagram showing an example of a control system of the optical image measuring apparatus according to the second embodiment of the present invention.

First, the optical image measuring apparatus according to this embodiment will be described. FIG. 6 illustrates (mainly) an optical system of the optical image measuring apparatus according to this embodiment and FIG. 7 illustrates a control system thereof. Hereinafter, the same reference numerals and symbols are provided to the same constituent portions as those in the first embodiment.

[Structure of Optical System]

Referring to FIG. 6, as in the first embodiment, an optical image measuring apparatus 100 according to this embodiment includes the light beam emitting portion 2, the lenses 4 and 5, the half mirror 6 (dividing means and superimposing means), the frequency shifter 8 (frequency shifting means), the reference mirror 9 (reference object), and the piezoelectric element 9A. The lenses 4 and 5 convert the light beam B from the light beam emitting portion 2 to a parallel light beam and increase a beam diameter thereof. The half mirror 6 divides the light beam B into the signal light S and the reference light R and superimposes the signal light S and the reference light R on each other to produce interference light M. The reference mirror 9 is a total reflection mirror. The piezoelectric element 9A is used to move the reference mirror 9 in the optical path direction of the reference light R.

As shown in FIG. 2 of the first embodiment, the light beam emitting portion 2 includes the broad-band light source 2A for outputting the light beam B1 having the (center) wavelength $\lambda 1$ and the broad-band light source 2B for outputting the light beam B2 having the wavelength $\lambda 2$. The piezoelectric element 9A also acts to vibrate the reference mirror 9.

The frequency of the reference light R may be shifted by the z-scanning of the reference mirror 9 instead of the frequency shifter 8 or in addition to the frequency shifter 8.

The optical image measuring apparatus 100 further includes the imaging lens group 10, the beam splitter 12 (optical path dividing means), the CCDs 21 and 22 (detecting means), and shutters 41 and 42. The imaging lens group 10 images the interference light M produced by the half mirror 6. The beam splitter 12 divides the interference light M into two interference light beams M1 and M2. Each of the CCDs 21 and 22 is the storage type two-dimensional photo sensor array for interference light beam detection. The shutters 41 and 42 are disposed immediately in front of the CCDs 21 and 22, respectively, and periodically cut off the interference light beams M1 and M2, respectively. Each of the shutters 41 and 42 is, for example, a high-speed shutter such as a liquid crystal shutter. Results obtained by detection with the CCDs 21 and 22 are outputted to the signal processing portion 20 (image forming means).

The shutters 41 and 42 are not necessarily disposed immediately in front of the CCDs 21 and 22, respectively. The shutters 41 and 42 can be disposed at arbitrary positions on respective optical paths joining branch points on which the interference light beams M1 and M2 are separated by the beam splitter 12 with the CCDs 21 and 22. That is, it is only necessary that the shutters 41 and 42 be disposed in positions in which the respective interference light beams M1 and M2 can be cut off or transmitted to change the quantities of light beams received by the CCDs 21 and 22 between 0 and 100.

The optical image measuring apparatus 100 further includes a pulse signal generator 50 and phase shifters 51 and 52. The pulse signal generator 50 generates pulse signals for driving shutter. The phase shifters 51 and 52 shift the phases of the pulse signals generated by the pulse signal generator 50 and output the pulse signals whose phases are shifted to each other to the shutters 41 and 42. The shutters 41 and 42 separately switch between cutting off and transmitting the interference light beams M1 and M2, respectively, in response to the pulse signals from the phase shifters 51 and 52 as timing signals.

The shutters 41 and 42 periodically cut off the interference light beams M1 and M2 at a predetermined frequency, respectively, in response to the timing signals from the phase shifters 51 and 52 to sample the respective interference light beams M1 and M2. Therefore, the CCDs 21 and 22 periodically receive the corresponding interference light beams M1 and M2, perform photoelectric conversion thereon, and output heterodyne signals which are results obtained by the conversion to the signal processing portion 20. As in the first embodiment, the signal processing portion 20 performs calculation processing described later and processing for forming an image of the object to be measured O.

The phase shifters 51 and 52 apply a predetermined phase difference between the open-and-close operations of the shutters 41 and 42. The phase difference may be, for example, 90° ($\pi/2$) as in the first embodiment or 180° ($\pi$) (can be arbitrarily set). Therefore, it is unnecessary to provide the phase shifter in front of each of the shutters 41 and 42. The phase shifter may be provided only in front of one of the shutters 41 and 42. For example, the phase shifter can be disposed only in front of not the shutter 41 but the shutter 42.

The shutters 41 and 42 compose "intensity modulating means" in the present invention. The intensity modulating means according to the present invention is not limited to the shutters for completely cutting off the interference light beams M1 and M2. For example, filters for transmitting 50% of the interference light beams M1 and M2 (50% in transmittance) can also be used. When such filters are inserted into and removed from the optical paths of the interference light beams M1 and M2, the intensity of each of the interference light beams M1 and M2 is modulated between 100% and 50%.

The beam diameter of the light beam B emitted from the light beam emitting portion 2 is increased by the lenses 4 and 5. Then, the light beam B is divided into the signal light S and the reference light R by the half mirror 6. The signal light S is incident on the object to be measured O and then incident on half mirror 6 again as a reflection light wave including information related to a surface structure and an internal structure of the object to be measured O.

On the other hand, the frequency of the reference light R is shifted by the frequency shifter 8. The reference light R whose frequency is shifted is incident on half mirror 6 again through the reference mirror 9 vibrated by the piezoelectric element 9A.

A part of the signal light S from the object to be measured O is reflected on the half mirror 6. Simultaneously, a part of the reference light R which is subjected to the frequency shift passes through the half mirror 6. Therefore, the signal light S and the reference light R are superimposed on each other by the half mirror 6 to produce the interference light M. The interference light M passes through the imaging lens group 10 and propagates to the beam splitter 12.

An optical path of the interference light M is divided into two by the beam splitter 12. The interference light beam M1 reflected on the beam splitter 12 is detected by the CCD 21 through the shutter 41. The interference light beam M2 passing through the beam splitter 12 is detected by the CCD 22 through the shutter 42.

It is desirable that a division ratio of the interference light beam M separated by the beam splitter 12, that is, an intensity ratio between the reflected interference light beam M1 and the transmitted interference light beam M2 be 1:1. Therefore, the intensity levels of the interference light beams M1 and M2 detected by the CCDs 21 and 22 are made equal to each other. This is suitable to perform the calculation processing described later. Note that the division ratio of the interference light beam M separated by the beam splitter 12 is not limited to this and thus can be set as appropriate.

The optical image measuring apparatus 100 further includes the light source 31, the beam splitter 32, a beam splitter 39, and the photo detector (PD) 34. The light source 31 is composed of, for example, a laser diode that emits laser light. The beam splitter 32 transmits a part of the laser light from the light source 31. The beam splitter 39 divides the laser light passing through the beam splitter 32 into first laser light propagating through the frequency shifter 8 and the reference mirror 9 and second laser light propagating to the reflecting mirror 33. Then, the beam splitter 39 superimposes the first laser light and the second laser light on each other to produce assistant interference light. The photo detector 34 receives the produced assistant interference light. Here, a distance between the beam splitter 39 and the reference mirror 9 and a distance between the beam splitter 39 and the reflecting mirror 33 are set substantially equal to each other.

The part of the laser light outputted from the light source 31 passes through the beam splitter 32 and is divided by the beam splitter 39 into the first laser light propagating to the reference mirror 9 and the second laser light propagating to the reflecting mirror 33.

The first laser light propagating on the optical path in the reference mirror 9 direction is subjected to frequency shift by the frequency shifter 8 and the reference mirror 9 moved by the piezoelectric element 9A and then incident on the beam splitter 39 again. At this time, the amount of frequency shift applied to the first laser light becomes equal to the amount of frequency shift applied to the reference light R.

On the other hand, the second laser light propagating on the optical path in the reflecting mirror 33 direction is reflected on the reflecting mirror 33 and then incident on the beam splitter 39 again.

A part of the first laser light which is reflected on the reference mirror 9 is reflected on the beam splitter 39 and propagates to the beam splitter 32. A part of the second laser light which is reflected on the reflecting mirror 33 passes through the beam splitter 39 and propagates to the beam splitter 32. At this time, both the first laser light and the second laser light are superimposed on each other by the beam splitter 39 to produce the assistant interference light. The assistant interference light has a beat frequency equal to that of the interference light M.

A part of the assistant interference light produced by the beam splitter 39 is reflected on the beam splitter 32 and received by the photo detector 34. The photo detector 34 outputs an electrical signal corresponding to the received part of the assistant interference light. The electrical signal has a direct current component and an alternating current component as in the case of the heterodyne signal expressed by the expression (1). As described above, a frequency of the alternating current component is equal to the beat frequency of the interference light M.

[Structure of Control System]

Next, the control system of the optical image measuring apparatus 100 will be described with reference to FIG. 7. The control system of the optical image measuring apparatus 100 includes the light source driving portion 35 for separately driving the broad-band light sources 2A and 2B of the light beam emitting portion 2, a display device 36 on which an image is displayed, the control portion 37 for controlling the respective portions of the apparatus, the signal processing portion 20 having the calculation portion 20A and the image forming portion 20B, and the CCDs 21 and 22.

The detection signal from the photo detector 34 and the image (image signal) formed by the signal processing portion 20 are inputted to the control portion 37.

The light source driving portion 35 generates the above-mentioned light source drive signals for separately driving the broad-band light sources 2A and 2B under the control of the control portion 37. Therefore, the light source driving portion 35 generates a pulse signal having a frequency synchronized with the frame rate based on the set information of the frame rate (frame interval) for the CCDs 21 and 22 which is set by the control portion 37. The pulse signal is used as the first light source drive signal for driving the broad-band light source 2A.

In addition, the light source driving portion 35 shifts the phase of the formed first light source drive signal by the amount of shift corresponding to the frame interval for the CCDs 21 and 22 to generate the second light source drive signal for driving the broad-band light source 2B. The light source driving portion 35 outputs the first light source drive signal and the second light source drive signal which are obtained as described above to the broad-band light source 2A of the light beam emitting portion 2 and the broad-band light source 2B thereof, respectively.

The optical image measuring apparatus 100 further includes a piezoelectric driver 38 for driving the piezoelectric element 9A and the pulse signal generator 50 for driving the shutters 41 and 42.

The piezoelectric driver 38 operates to generate an electrical signal which has a frequency synchronized with the electrical signal (for example, a frequency equal to that of the electrical signal) outputted from the photo detector 34 and an amplitude in which the amplitude of vibration of the piezoelectric element 9A is ½ of the wavelength of the electrical signal therefrom and to output the generated electrical signal to the piezoelectric element 9A under the control of the control portion 37. Assume that a relationship between the amplitude of the electrical signal sent to the piezoelectric element 9A and the amplitude of vibration of the piezoelectric element 9A is known. The piezoelectric driver 38 outputs the electrical signal having the amplitude obtained based on the relationship to the piezoelectric element 9A. Therefore, the reference mirror 9 is vibrated at the frequency synchronized with the frequency of the interference light M with the amplitude equal to ½ of the wavelength of the interference light M.

The pulse signal generator 50 generates pulse signals having a frequency synchronized with the electrical signal outputted from the photo detector 34 (for example, a frequency equal to that of the electrical signal) under the control of the control portion 37 and outputs the generated pulse signals to the phase shifters 51 and 52. The phase shifters 51 and 52 shift the phases of the pulse signals relative to each other and output the pulse signals whose phases are shifted relative to each other to the shutters 41 and 42. The shutters 41 and 42 are driven based on the pulse signals whose phases are shifted relative to each other and repeat the open-and-close operation at a frequency equal to that of the pulse signals. Therefore, the CCDs 21 and 22 receive the interference light beams M1 and M2 at the frequency synchronized with the frequency of the interference light M.

[Measurement Mode]

Subsequently, a measurement mode for the image of the object to be measured O, which is obtained by the optical image measuring apparatus 100 according to this embodiment will be described. Hereinafter, the measurement principle of the optical image measuring apparatus 100 will be first described and processing for imaging the functional information on a living tissue will then be described.

The laser light emitted from the light source 31 is divided by the beam splitter 39 into an optical path in the reference mirror 9 direction and an optical path in the reflecting mirror 33 direction. The laser light beams are superimposed on each other by the beam splitter 39 to produce the assistant interference light. The assistant interference light is received by the photo detector 34. The photo detector 34 outputs an electrical signal having a frequency synchronized with the frequency of the received assistant interference light.

The pulse signal generator 50 generates the pulse signals having the frequency synchronized with the electrical signal from the photo detector 34 in response to the electrical signal and transmit the generated pulse signals to the phase shifters 51 and 52. The phase shifters 51 and 52 shift the phases of the pulse signals relative to each other and output the pulse signals whose phases are shifted relative to each other to the shutters 41 and 42. Each of the shutters 41 and 42 switches between open operation and close operation at the frequency of the pulse signals.

The piezoelectric driver 38 generates the electrical signal which has the frequency synchronized with the electrical signal from the photo detector 34 and the amplitude in which the amplitude of vibration of the piezoelectric element 9A becomes ½ of the wavelength of the electrical signal therefrom. The piezoelectric driver 38 outputs the generated electrical signal to the piezoelectric element 9A. Therefore, the reference mirror 9 is vibrated by the piezoelectric element 9A at the frequency synchronized with the frequency of the interference light L with the amplitude equal to ½ of the wavelength of the interference light L. The amplitude of vibration of the reference mirror 9 is not limited to ½ of the wavelength of the interference light L and thus can be arbitrarily set.

As described above, in this embodiment, the amount of frequency shift which is applied to the reference light R is monitored. The shutters 41 and 42 are opened and closed at the frequency synchronized with the amount of frequency shift (=the frequency of the interference light L) to sample the interference light beams M1 and M2. In addition, the reference mirror 9 is vibrated at the frequency synchronized with the interference light L with the amplitude equal to ½ of the wavelength of the interference light L.

A sampling function $m_1(t)$ for controlling the open-and-close timings of the shutter 41 is composed of, for example, a signal train of a rectangular wave with a duty of 50%. When the center wavelength of the laser light from the light source 31 is substantially equal to that of the light beam B from the light beam emitting portion 2, a frequency (sampling frequency) $f_{sm}$ of the sampling function $m_1(t)$ becomes a value equal to or close to the beat frequency $f_{if}$ indicated in the expression (1) (that is, $f_{sm} = f_{if}$ or $f_{sm} \approx f_{if}$). A difference between the frequency $f_{sm}$ of the sampling function $m_1(t)$ and the beat frequency $f_{if}$ of the heterodyne signal which is indicated in the expression (1) is expressed by ($\delta f = |f_{if} - f_{sm}|$) The difference $\delta f$ is set to a value sufficiently smaller than a response frequency of the CCD 21. Therefore, a part of the interference light beam M1 having substantially the same phase is sampled during each period thereof. At this time, an output $i_1(t)$ from the CCD 21 that receives the interference light beam M1 is proportional to the amount of photo charge stored in the CCD 21 during a measurement period. More specifically, the output $i_1(t)$ is expressed by the following expression (for example, see M. Akiba, K. P. Chan, and N. Tanno, Optics Letters, Vol. 28, 816 (2003)).

$$i_1(t) = \langle K_1 i(t) m_1(t) \rangle \quad (21)$$

$$= K_1 \left[ \frac{1}{2} I_s + \frac{1}{2} I_r + \frac{2}{\pi} \sqrt{I_s I_r} \cos(2\pi\delta f t + \phi) \right]$$

Here, <-> indicates a time average produced by a storage effect of the CCD 21. In addition, Φ indicates an initial phase value for measurement and $K_1$ indicates photo detection efficiency including reflectance of the beam splitter 12 and a photoelectric conversion rate of the CCD 21.

Similarly, the interference light beam M2 is sampled by the shutter 42 whose open-and-close timings are controlled using a sampling function $m_2(t)$ based on the pulse signal outputted from the pulse signal generator 50 at the frequency $f_{sm}$. The interference light beam M2 which is sampled by the shutter 42 is detected by the CCD 22. The sampling function $m_2(t)$ has a waveform of a rectangular train with a duty of 50% and the frequency $f_{sm}$ thereof is equal to that of the sampling function $m_1(t)$ for sampling the interference light beam M1. The sampling function $m_2(t)$ has a phase difference $\Delta\theta_{1,2}$ (for example, 180° or 90°) with the sampling function $m_1(t)$. The phase difference $\Delta\theta_{1,2}$ is produced by setting the amount of phase shifts applied by the phase shifters 51 and 52 in advance. Under the above-mentioned condition, the following output $i_2(t)$ is obtained from the CCD 22 based on the same principles as the expression (21).

$$i_2 = K_2 \left[ \frac{1}{2} I_s + \frac{1}{2} I_r + \frac{2}{\pi} \sqrt{I_s I_r} \cos(2\pi\delta f t + \phi + \Delta\theta_{1,2}) \right] \quad (22)$$

Here, $K_2$ indicates photo detection efficiency including the transmittance of the beam splitter 12 and a photoelectric conversion rate of the CCD 22.

As is apparent from the expressions (21) and (22), each of the outputs from the CCDs 21 and 22 includes the term of an intensity $I_s$ of the signal light S and the term of an intensity $I_r$ of the reference light R. In addition, the output from the CCD 21 includes the term related to an amplitude $\sqrt{(I_s I_r)}$ of the interference light beam M1 and a phase $(2\pi\delta f t+\Phi)$ thereof. The output from the CCD 22 includes the term related to an amplitude $\sqrt{(I_s I_r)}$ of the interference light beam M2 and a phase $(2\pi\delta f t+\Phi+\Delta\theta_{1,2})$ thereof.

Figure 8A:
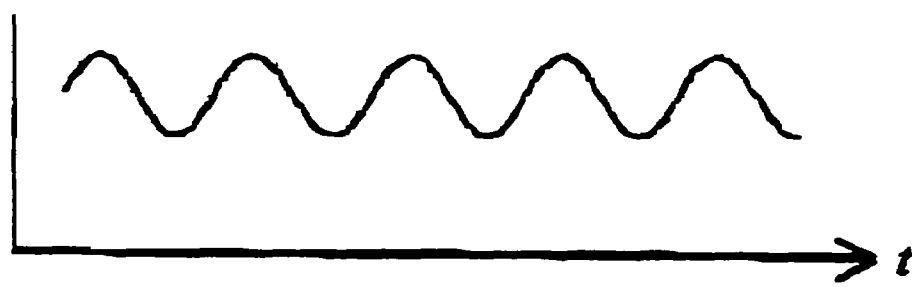
Figure 8B:
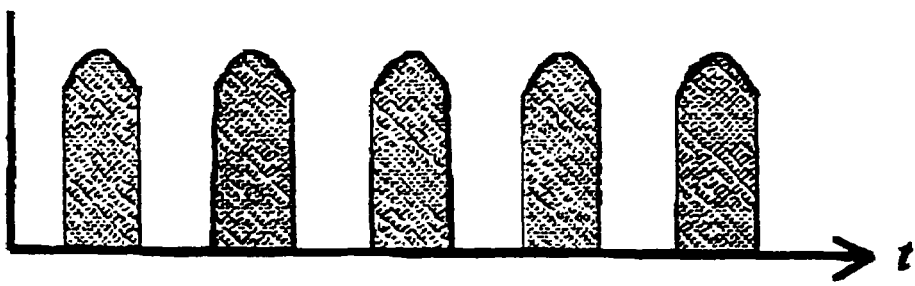
Figure 8C:
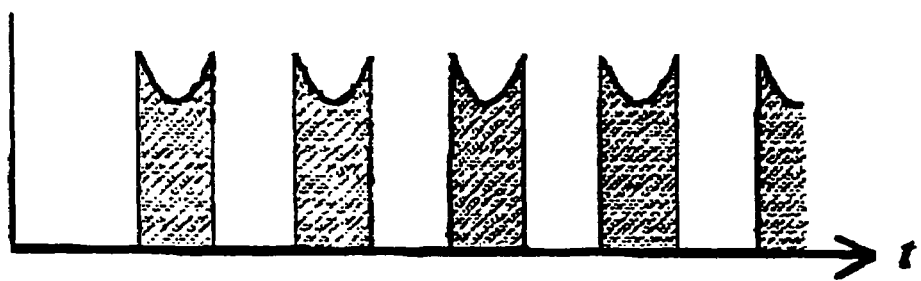
Figure 10:
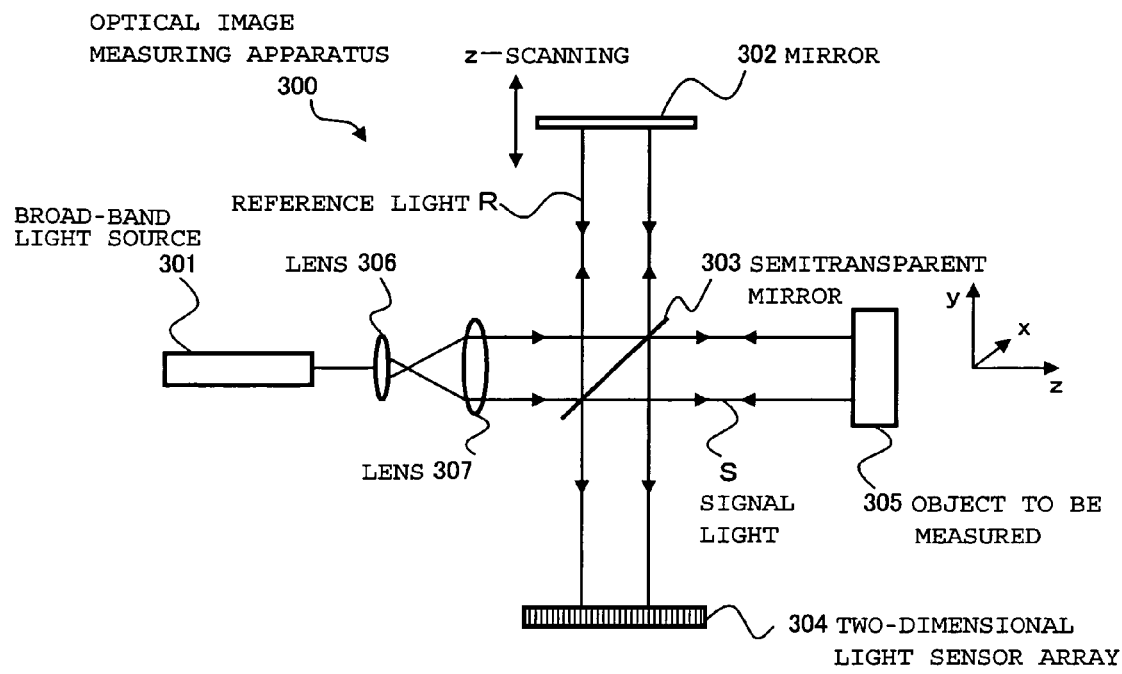
FIG. 10 is a schematic diagram showing a conventional optical image measuring apparatus.

FIGS. 8A to 8C are explanatory diagrams showing sampling operations of the interference light beams M1 and M2 which are performed by the shutters 41 and 42 in the case where the phase difference $\Delta\theta_{1,2}$ between the sampling functions $m_1(t)$ and $m_2(t)$ with the duty of 50% is set to 180° (π). FIG. 8A illustrates a time waveform of the interference light M. FIG. 8B illustrates a time waveform of the interference light beam M1 received by the CCD 21 through the shutter 41. FIG. 8C illustrates a time waveform of the interference light beam M2 received by the CCD 22 through the shutter 42.

As is apparent from FIGS. 8A to 8C, when the phase of the interference light M is 0°, the shutter 41 is opened. In addition, when the phase of the interference light M is 180°, the shutter 41 is closed. Therefore, a part of the interference light beam M1 (interference light M) corresponding to a phase range of 0° to 180° is detected by the CCD 21. On the other hand, when the phase of the interference light M is 180°, the shutter 42 is opened. In addition, when the phase of the interference light M is 360° (=0°), the shutter 42 is closed. Therefore, a part of the interference light beam M2 (interference light M) corresponding to a phase range of 180° to 360° is detected by the CCD 22.

In order to obtain a high-precision image, as shown in FIG. 8B, it is preferable that the interference light beam M1 detected by the CCD 21 include a "peak" part of the interference light beam Ml, that is, a part in which the intensity thereof is maximum. In addition to this, as shown in FIG. 8C, it is preferable that the interference light beam M2 detected by the CCD 22 include a "valley" part of the interference light beam M2, that is, a part in which the intensity thereof is minimum. In contrast to this, a "valley" part of the interference light beam M1 and a "peak" part of the interference light beam M2 may be detected.

The calculation portion 20A of the signal processing portion 20 calculates a spatial signal intensity distribution of the interference light M and a spatial phase distribution thereof based on results obtained by detection with the CCDs 21 and 22. The image forming portion 20B forms images corresponding to the results obtained by detection with the CCDs 21 and 22 based on a result obtained by calculation in the calculation portion 20A. In addition, the image forming portion 20B subtracts the images from each other to form an image showing the intensity distribution of the interference light M or the phase distribution thereof, that is, an image showing a surface structure of the object to be measured O or an internal structure thereof. The formed image is outputted as an image signal from the control portion 37 to the display device 36 and displayed thereon.

[Imaging of Functional Information on Living Tissue]

A measurement mode in the present invention, that is, processing for forming an image including functional information on a living tissue, which is executed based on the measurement principle of the optical image measuring apparatus 100 will be described. The following calculation processing is executed by the calculation portion 20A of the signal processing portion 20 and image forming processing based on a result obtained by the calculation processing is executed by the image forming portion 20B.

Hereinafter, the oxygen saturation of hemoglobin is considered as an example of the functional information on the living tissue. As in the first embodiment, assume that each of the (center) wavelengths λ1 and λ2 of the light beams B1 and B2 is set to the vicinity of the frequency at which the absorption characteristic of the oxyhemoglobin and the absorption characteristic of the deoxyhemoglobin intersect. For example, the wavelength λ1 of the light beam B1 is set to a wavelength at which the light beam B1 is more absorbed by the oxyhemoglobin (for example, 840 nm). In addition, the wavelength λ2 of the light beam B2 is set to a wavelength at which the light beam B2 is more absorbed by the deoxyhemoglobin (for example, 760 nm).

The optical image measuring apparatus 100 selectively outputs one of the light beam B1 having the wavelength λ1 and the light beam B2 having the wavelength λ2 at a frequency synchronized with the frame rate for the CCDs 21 and 22, thereby obtaining images corresponding to the respective wavelengths.

Assume that the maximum intensities of the light beams B1 and B2 are equal to each other and an intensity of the signal light S incident on the object to be measured (living tissue) O is expressed by $I_{in}$. In addition, assume that a scattering and absorption coefficient of the object to be measured O is expressed by $\sigma=\sigma(\lambda)$ and a depth at which the signal light S interfering with the reference light R is reflected in the object to be measured O (that is, half of the distance which the signal light S involved in producing the interference light M propagates through the object to be measured O) is expressed by 1. At this time, an intensity $I_{out,1}$ of the signal light S based on the laser beam B1, which exits from the object to be measured O and an intensity $I_{out,2}$ of the signal light S based on the laser beam B2, which exits from the object to be measured O are expressed by the above-mentioned expressions (16) and (17). A relationship expressed by an expression (20) is obtained from the expressions (16) and (17).

Thus, as in the first embodiment, the optical image measuring apparatus 100 can form an image showing the distribution of the scattering and absorption coefficient in the object to be measured (living tissue) O. The distribution image of the scattering and absorption coefficient shows the distribution state of the oxygen saturation of hemoglobin in the object to be measured O.

[Operation and Effect]

As described above, according to the optical image measuring apparatus 100 in this embodiment, the two-dimensional image of the object to be measured O at a depth thereof can be obtained without scanning the object to be measured O with the signal light S. In addition, the three-dimensional image of the object to be measured O can be obtained by only the z-scanning of the reference mirror 9. Therefore, it is possible to efficiently form an image expressing the oxygen saturation of hemoglobin.

When the wavelengths λ1 and λ2 of the light beams B1 and B2 alternately outputted by switching are arbitrarily set for any purpose, an image expressing other functional information on the living tissue can be efficiently obtained.

[Modified Examples]

The optical image measuring apparatus 100 described above divides the interference light into two light interference beams to separately detect the light interference beams. The number of optical paths of interference light beams into which the interference light is divided is arbitrary. For example, as described in Japanese Patent Application No. 2004-100741 which is made by the inventors of the present invention, interference light can be divided into three interference light beams to separately detect the light interference beams. In this case, the detecting means (CCD) is provided on each of the optical paths of the separated interference light beams. The intensity modulating means (shutter) for modulating the intensity of the interference light beam is provided on each of some of the optical paths of the separated interference light beams. For example, when detecting means for measuring only the intensity of background light (direct current component) of the interference light beam is provided, it is unnecessary to dispose the intensity modulating means in front of the detecting means.

In the present invention, the structure for vibrating the reference mirror 9 is not essential. For example, when the interference light is divided into three or more optical paths to detect interference light beams, the structure is unnecessary.

As described in the modified examples of the first embodiment, a structure including the light beam cutoff means can be also used as the structure for alternately outputting the light beams B1 and B2.

Various Modified Examples

The above-mentioned detailed embodiments are merely examples for embodying the optical image measuring apparatus according to the present invention. Therefore, arbitrary modifications can be made without departing from the spirit of the present invention.

The number of broad-band light sources included in the light beam emitting portion 2 is arbitrary. In general, "n" broad-band light sources 2-1, 2-2, ..., 2-n can be provided in the light beam emitting portion $\mathbf{2}(n \geq 2)$. The broad-band light sources 2-1 to 2-n output light beams having different center-wavelengths (some light beams may have the same wavelength). Therefore, it is possible to form an image expressing plural types of functional information on a living tissue. That is, in each of the above-mentioned embodiments, only an image expressing one type of functional information (oxygen saturation of hemoglobin) can be obtained because the two light beams having different wavelengths are used. However, three or more light beams having different wavelengths are used, so an image expressing two or more types of functional information can be obtained.

The method of selectively outputting one of the plurality of light beams having different wavelengths is not limited to the method of pulse-driving the light source and the method of periodically cutting off one of the light beams using the shutters. Therefore, arbitrary methods can be applied.

What is claimed is:

1. An optical image measuring apparatus, comprising:

light beam outputting means for selectively outputting one of a plurality of light beams having different wavelengths, intensities of the light beams being periodically modulated;

first converting means for converting a polarization characteristic of the outputted one of the light beams to linear polarization;

dividing means for dividing the outputted one of the light beams into signal light propagating through an object to be measured and reference light propagating through a reference object;

second converting means for converting a polarization characteristic of one of the signal light and the reference light, which is the linear polarization;

frequency shifting means for shifting a frequency of the signal light and a frequency of the reference light relative to each other;

superimposing means for superimposing the signal light propagating through the object to be measured and the reference light propagating through the reference object on each other to produce interference light, each of the signal light and the reference light including a polarization characteristic converted by the first converting means and the second converting means, the frequency of the signal light and the frequency of the reference light being shifted by the frequency shifting means;

extracting means for extracting a plurality of polarized light components from the produced interference light, the polarized light components being different from one another;

two-dimensional detection means for detecting each of the polarized light components extracted from the interference light; and image forming means for forming an image of a distribution of oxygen saturation of the object to be measured by determining state information of the light with respect to each of at least two light beams of the plurality of light beams having the different wavelengths, wherein the scattering and absorption coefficients of the object are used together for the image formation.

2. An optical image measuring apparatus according to claim 1, wherein:

each of the light beams is periodically outputted from the light beam outputting means;

the result is obtained by the two-dimensional detection means at a predetermined time interval; and a period for which each of the light beams is outputted is synchronized with the predetermined time interval at which the result is obtained by the two-dimensional detection means.

3. An optical image measuring apparatus according to claim 2, further comprising calculating means for calculating one of an intensity and a phase of the interference light beam based on the result obtained by the two-dimensional detection means, wherein the image of the object to be measured is formed based on the calculated one of the intensity and the phase of the interference light beam.

4. An optical image measuring apparatus according to claim 3, wherein:

the object to be measured comprises a living tissue;

the at least two light beams comprise a first light beam including a center wavelength of a wavelength region in which an amount of absorption of oxyhemoglobin is larger than an amount of absorption of deoxyhemoglobin, and a second light beam having a center wavelength of a wavelength region in which the amount of absorption of the deoxyhemoglobin is larger than the amount of absorption of the oxyhemoglobin; and the image forming means forms an image expressing a distribution of oxygen saturation of hemoglobin in the living tissue based on a result obtained by the two-dimensional detection means with respect to the interference light beam caused from the first light beam and a result obtained by the two-dimensional detection means with respect to the interference light beam caused from the second light beam.

5. An optical image measuring apparatus according to claim 1, wherein the light beam outputting means comprises:

a plurality of light sources for emitting the light beams having the different wavelengths; and light source driving means for separately driving one of the plurality of light sources to switch among the light beams to be outputted.

6. An optical image measuring apparatus according to claim 2, wherein the light beam outputting means comprises:

a plurality of light sources for emitting the light beams having the different wavelengths; and light source driving means for separately driving one of the plurality of light sources to switch among the light beams to be outputted.

7. An optical image measuring apparatus according to claim 1, wherein the light beam outputting means comprises:

a plurality of light sources for emitting the light beams having the different wavelengths; and light beam cutoff means for selectively cutting off one of the light beams emitted from the plurality of light sources to switch among the light beams to be outputted.

8. An optical image measuring apparatus according to claim 2, wherein the light beam outputting means comprises:

a plurality of light sources for emitting the light beams having the different wavelengths; and light beam cutoff means for selectively cutting off one of the light beams emitted from the plurality of light sources to switch among the light beams to be outputted.

9. An optical image measuring apparatus according to claim 1, further comprising calculating means for calculating one of an intensity and a phase of the interference light beam based on the result obtained by the two-dimensional detection means, wherein the image of the object to be measured is formed based on the calculated one of the intensity and the phase of the interference light beam.

10. An optical image measuring apparatus according to claim 5, further comprising calculating means for calculating one of an intensity and a phase of the interference light beam based on the result obtained by the two-dimensional detection means, wherein the image of the object to be measured is formed based on the calculated one of the intensity and the phase of the interference light beam.

11. An optical image measuring apparatus according to claim 6, further comprising calculating means for calculating one of an intensity and a phase of the interference light beam based on the result obtained by the two-dimensional detection means, wherein the image of the object to be measured is formed based on the calculated one of the intensity and the phase of the interference light beam.

12. An optical image measuring apparatus according to claim 7, further comprising calculating means for calculating one of an intensity and a phase of the interference light beam based on the result obtained by the two-dimensional detection means, wherein the image of the object to be measured is formed based on the calculated one of the intensity and the phase of the interference light beam.

13. An optical image measuring apparatus according to claim 8, further comprising calculating means for calculating one of an intensity and a phase of the interference light beam based on the result obtained by the two-dimensional detection means, wherein the image of the object to be measured is formed based on the calculated one of the intensity and the phase of the interference light beam.

14. An optical image measuring apparatus according to claim 1, wherein:

the object to be measured comprises a living tissue;

the at least two light beams comprise a first light beam including a center wavelength of a wavelength region in which an amount of absorption of oxyhemoglobin is larger than an amount of absorption of deoxyhemoglobin, and a second light beam having a center wavelength of a wavelength region in which the amount of absorption of the deoxyhemoglobin is larger than the amount of absorption of the oxyhemoglobin; and the image forming means forms an image expressing a distribution of oxygen saturation of hemoglobin in the living tissue based on a result obtained by the two-dimensional detection means with respect to the interference light beam caused from the first light beam and a result obtained by the two-dimensional detection means with respect to the interference light beam caused from the second light beam.

15. An optical image measuring apparatus according to claim 2, wherein:

the object to be measured comprises a living tissue;

the at least two light beams comprise a first light beam including a center wavelength of a wavelength region in which an amount of absorption of oxyhemoglobin is larger than an amount of absorption of deoxyhemoglobin, and a second light beam having a center wavelength of a wavelength region in which the amount of absorption of the deoxyhemoglobin is larger than the amount of absorption of the oxyhemoglobin; and the image forming means forms an image expressing a distribution of oxygen saturation of hemoglobin in the living tissue based on a result obtained by the two-dimensional detection means with respect to the interference light beam caused from the first light beam and a result obtained by the two-dimensional detection means with respect to the interference light beam caused from the second light beam.

16. An optical image measuring apparatus according to claim 9, wherein:

the object to be measured comprises a living tissue;

the at least two light beams comprise a first light beam including a center wavelength of a wavelength region in which an amount of absorption of oxyhemoglobin is larger than an amount of absorption of deoxyhemoglobin, and a second light beam having a center wavelength of a wavelength region in which the amount of absorption of the deoxyhemoglobin is larger than the amount of absorption of the oxyhemoglobin; and the image forming means forms an image expressing a distribution of oxygen saturation of hemoglobin in the living tissue based on a result obtained by the two-dimensional detection means with respect to the interference light beam caused from the first light beam and a result obtained by the two-dimensional detection means with respect to the interference light beam caused from the second light beam.

17. An optical image measuring apparatus according to claim 1, wherein:

the image forming means is configured to determine, as the items of the state information, an intensity of incident signal light and an intensity of exit signal light, with respect to the light beam of the different wavelengths based on the polarized light component, so as to use the intensity of the incident signal light and the intensity of the exit signal light with respect to each of the light beams of the different wavelengths to form an image of a distribution indicating oxygen saturation of the object to be examined.

* * * * *